United States Patent
McLeod

(10) Patent No.: US 10,900,944 B1
(45) Date of Patent: Jan. 26, 2021

(54) SENSOR CLEANING AND CALIBRATION DEVICES AND SYSTEMS

(71) Applicant: Marmac Water LLC, Greenwood Village, CO (US)

(72) Inventor: Gregg Allan McLeod, Greenwood Village, CO (US)

(73) Assignee: Marmac Water LLC, Greenwood Village, CO (US)

( * ) Notice: Subject to any disclaimer, the term of this patent is extended or adjusted under 35 U.S.C. 154(b) by 0 days.

(21) Appl. No.: 16/894,233

(22) Filed: Jun. 5, 2020

Related U.S. Application Data

(60) Provisional application No. 62/995,873, filed on Feb. 18, 2020, provisional application No. 62/921,821, filed on Jun. 7, 2019.

(51) Int. Cl.
*G01N 33/18* (2006.01)
*G01N 35/10* (2006.01)
*G01N 35/00* (2006.01)
*G01N 1/20* (2006.01)

(52) U.S. Cl.
CPC ..... *G01N 33/1893* (2013.01); *G01N 33/1886* (2013.01); *G01N 35/00623* (2013.01); *G01N 35/00693* (2013.01); *G01N 35/1004* (2013.01); *G01N 35/1097* (2013.01); *G01N 2001/205* (2013.01); *G01N 2001/2064* (2013.01)

(58) Field of Classification Search
CPC ..... G01N 2001/205; G01N 2001/2064; G01N 35/1095; G01N 35/1097; G01N 33/1893; G01N 33/1886; G01N 35/00693
See application file for complete search history.

(56) References Cited

U.S. PATENT DOCUMENTS

| | | | | |
|---|---|---|---|---|
| 3,913,384 A * | 10/1975 | Furuya | ................... | G01N 33/18 73/53.01 |
| 4,385,936 A * | 5/1983 | Rossi | ................... | B08B 3/02 134/18 |
| 4,447,309 A * | 5/1984 | Morioka | ............ | G01N 27/4035 204/402 |
| 5,249,464 A * | 10/1993 | Brown | ................... | G01F 1/06 116/276 |
| 5,817,231 A * | 10/1998 | Souza | ................... | B01D 61/08 210/96.2 |
| 2007/0263046 A1 | 11/2007 | Iwasa et al. | | |

(Continued)

FOREIGN PATENT DOCUMENTS

WO   2018/116186 A1   6/2018

OTHER PUBLICATIONS

International Search Report for PCT Application PCT/US2020/036365, dated Sep. 3, 2020 (24 pages).

*Primary Examiner* — Paul M. West
(74) *Attorney, Agent, or Firm* — Sheridan Ross P.C.

(57) ABSTRACT

An electrode cleaning and calibration system generally comprises a sensor holder assembly machined from a block of solid acrylic or similar plastic material, which can accommodate a variety of types and sizes of sensors for use in monitoring and measurement of water processing and treatment processes. Examples of sensors suitable for use in the system include pH sensors, dissolved oxygen sensors, chlorine sensors, ozone sensors, total suspended solid sensors, mixed liquor suspended solid sensors, ammonia sensors, monochloramine sensors, and ultraviolent transmittance sensors.

12 Claims, 19 Drawing Sheets

(56) References Cited

U.S. PATENT DOCUMENTS

2010/0288023 A1 11/2010 Leyer et al.
2013/0192337 A1 8/2013 Ashton et al.
2018/0136247 A1 5/2018 Boutelle et al.

* cited by examiner 641
642

643

SENSOR CLEANING AND CALIBRATION DEVICES AND SYSTEMS

CROSS-REFERENCE TO RELATED APPLICATIONS

This application claims the benefit of priority of U.S. Provisional Patent Application 62/995,873, filed 18 Feb. 2020, and U.S. Provisional Patent Application 62/921,821, filed 7 Jun. 2019, the entireties of both of which are incorporated herein by reference.

FIELD OF THE INVENTION

The present invention relates generally to devices and systems for holding, cleaning, and calibrating analytical sensors, and particularly to such devices and systems in which the sensors can be held, inspected, cleaned, and/or calibrated in either a manual mode or an automated mode without the need to remove the sensors from the device or system.

BACKGROUND OF THE INVENTION

To maintain and verify accurate water quality and process performance and comply with regulatory requirements, water processing and treatment facilities (e.g. municipal drinking water and wastewater facilities and water processing units in food processing plants, chemical processing plants, refineries, industrial plants, etc.) may utilize analytical sensors to measure any one or more of a wide array of variables, including but not necessarily limited to pH, dissolved oxygen content, ammonia content, chlorine content, monochloramine content, ozone content, total suspended solid content, mixed liquor suspended solid content, and ultraviolet transmittance. These measurements require the use of sensitive in-line sensors that employ various sensing methods to measure and monitor a variable of interest, but in general, such sensors comprise an electrode including a sensitive glass membrane or other sensing tip. In most or all cases, accumulation of foreign material on the sensor electrode will impair the accuracy of the sensor; thus, the sensor electrode must remain clean and free of accumulated contaminants to consistently provide accurate measurement, which in turn is essential to reliable analysis of the water being processed or treated and thus to the function of the overall water processing or treatment facility.

Currently, the recommended maintenance regiment for conventional sensor systems includes manual retrieval, cleaning, and calibration of the individual sensors on a regular basis. In some cases, such maintenance must be carried out daily or even more frequently, depending on the quality of the water being treated, to satisfy regulatory requirements and/or maintain the accuracy of the sensor.

While some methods and systems have been developed that enable automated cleaning of sensors to prevent accumulation of foulants, such devices are generally configured to employ only a single cleaning function, or in some cases dual cleaning functions, which is typically inadequate to prevent accumulation of the full array of foulants that may be encountered. For example, many such methods and systems employ only an air burst or water jet (or in some cases both) to maintain the cleanliness of the electrode and/or sensor surface, which may fail to remove many types of organic or inorganic contaminant. Thus, even those systems employing an automated cleaning function require periodic manual cleaning to remove those foulants not removed, or not completely removed, by an air burst and/or water jet.

Additional complications and drawbacks of existing automated sensor cleaning methods and systems include the fact that such methods and systems are generally ineffective to clean the sensor while the sensor is submerged in the aqueous analyte stream. Cleaning of sensors by water jetting or aeration is ineffective or less effective when carried out underwater, and cleaning treatments that utilize a rinse or soak of the sensor in a foreign chemical (e.g. acid or hot water) are not feasible unless the sensor is physically removed from the aqueous analyte stream. Ultrasonic cleaning is likewise ineffective when the sensor is positioned in water, as sonic waves generated by a transducer dissipate through the aqueous stream and away from the targeted sensor.

Many water treatment facilities employ methods or systems that facilitate side-stream flow through a sensor holder, which allows for easier access to retrieve the sensor/electrode for cleaning and/or calibration. While such systems improve the ease of cleaning and calibration, whether in a manual or automated mode, such methods and systems still require retrieval of the sensor/electrode before it can be cleaned and/or calibrated.

There is thus a need in the art for sensor holder assemblies that allow for a multitude of sensor cleaning functions and techniques to be employed, and for devices, methods, and systems incorporating such assemblies. It is further advantageous for such devices, methods, and systems to enable any one or more of (1) bypass of the sensor by the aqueous analyte stream to isolate the sensor; (2) cleaning and calibration of the sensor without removal from the water processing or treatment system; (3) visual inspection of the sensor and/or electrode before, during, or after operation; (4) automated cleaning and calibration without human intervention; and (5) durability against the effects of caustic agents, strong acids, and other potentially damaging chemical agents.

SUMMARY OF THE INVENTION

Embodiments and configurations of the present disclosure can address these and other needs.

Devices, methods, and systems of the present invention include features that enable and/or provide for any one or more of a multitude of functions for cleaning sensors and/or electrodes, which may in embodiments include spraying or rinsing with cold or hot water, an acid, an oxidizer, a surfactant, an enzyme, or another chemical cleaning agent, or ultrasonic cleaning. Sensor holder assemblies according to the present invention are generally manufactured from a block of acrylic or similar plastic materials that are resistant to acids, oxidants, and other potentially damaging chemicals that may be used in the cleaning and calibration process, and may in embodiments be fitted with a magnifying lens, one or more light-emitting diodes (LEDs), or other similar means for allowing a technician or user to visually inspect the sensors or portions thereof. In some embodiments, the devices, methods, and systems of the invention may include a programmable logic controller (PLC) that may include software enabling such functions as automated cleaning or calibration of one or more sensors and/or alternating sampling logic that allows for analysis of an aqueous analyte stream at multiple points.

Sensor holder assemblies of the present invention may be configured to cause an aqueous analyte stream to bypass the sensor, thus isolating the sensor/electrode to allow for, e.g., improved soaking or rinsing of the electrode to remove foulants. Such a bypass may provide various other advantages as well, such as the ability to calibrate the sensors (using a buffer solution or other standard reference material) or provide an ultrasonic cleaning function without removing the electrode(s)/sensor(s) from the holder assembly.

Another advantage of the present invention is that it may enable a user or technician to visually inspect the electrode itself during both normal operation and a cleaning or calibration procedure. Particularly, because sensor holder assemblies of the present invention may be manufactured from a transparent or translucent material, such as a transparent or translucent solid block of acrylic or similar plastic, a technician can inspect the electrode without removing the electrode from the holder. In embodiments, the sensor holder assembly may include a magnifying lens opposite the electrode sensor and/or one or more LEDs to improve the visibility of the electrode/sensor to the technician. One or more LEDs (which may be the same as or different from LEDs used to improve the visibility of the electrode/sensor) may also be configured to provide a visual indicator (e.g. by blinking or changing color) of cleaning or calibration status or a fault condition.

Embodiments of the invention include, or are adapted to work in conjunction with, a computerized system to activate and automate desired cleaning and calibration functions. By way of non-limiting example, a master control panel may be fitted with either a programmable logic controller (PLC) or a microprocessor that includes software for scheduling, initiating, and carrying out cleaning and calibration functions. Such PLC or microprocessor may enable additional functions, such as a time delay to ensure that the electrode is not actively monitoring the aqueous analyte stream (and/or that data acquired by the sensor are not registered or recorded) during the cleaning or calibration procedure. In other embodiments, such as those in which the cost of an automated system is prohibitive, sensor holder assemblies of the invention may be provided without a computerized operating system, in which case the assembly may be fitted with (1) a Luer lock or similar fitting that allows attachment of a laboratory syringe so that a technician can manually inject materials for cleaning and calibrating the sensors and/or (2) an internal chemical distribution manifold machined within the holder assembly. Either of these features may allow for cleaning and calibration of sensors without the need to remove the sensors or the electrodes thereof from the assembly or provide a separate external manifold, and may improve safety by limiting the exposure of human users or technicians to cleaning and calibration materials.

Embodiments of the present invention include complete, automated systems for cleaning and calibrating sensors, and particularly sensor electrodes, in water processing and treatment systems, and particularly include systems that reduce the labor required to clean and calibrate sensors, improve the safety of technicians and users by limiting their exposure to potentially hazardous cleaning and calibration materials, and allow the sensors to consistently provide accurate and reliable measurements. Such systems can accommodate a wide range of analytical sensors, and can operate across a wide range of water quality conditions and/or in a "bypass" or "pass-through" mode by providing a continuous stream of fluid via one or more of gravity and pumping. In some embodiments, sensor holder assemblies of the present invention can accommodate a plurality of sensor cleaning methods, which may be selected from the group consisting of spraying or rinsing with cold or hot water, spraying or soaking with an acid, spraying or soaking with a surfactant, spraying or soaking with an oxidizer, spraying or soaking with an enzyme, spraying or soaking with another chemical cleaning agent, or ultrasonic cleaning. Some embodiments include a programmable logic controller (PLC) or microprocessor that includes software allowing for scheduling of sensor cleaning and calibration functions, timing of cleaning or calibrating steps, and logging and storing information relating to the sensor generally and/or the electrode specifically. Sensor holder assemblies can be manufactured from a single solid block of acrylic or similar plastic material, and may be configured to house one sensor/electrode or more than one sensor/electrode. In the case of embodiments including or adapted to operate in conjunction with dissolved oxygen sensors particularly, the invention may include an automated alternating sampling process that provides the sensor with samples of mixed liquor or other liquid analyte from various zones an aeration basin at various times, thereby eliminating the need for multiple sensors to monitor the different zones of the aeration basin. Advantageously, the devices, methods, and systems of the present invention may include features that make the invention particularly applicable to systems that receive, process, and/or treat especially dirty or contaminated aqueous streams.

Embodiments of the present invention may advantageously improve the visibility of the sensor or electrode itself to a user or technician, and/or may provide to a user or technician clear visual indicia of the status of the sensor/electrode and/or a cleaning or calibration process. By way of non-limiting example, some embodiments allow a user or technician to visually inspect a sensor without removing the sensor from the sensor holder assembly by providing within the sensor holder assembly one or both of a magnifying lens or LED lighting. One or more LEDs (which may be the same as or different from LEDs provided to allow the user or technician to visually inspect the electrode) can be included to provide a visual indicator—e.g. blinking, flashing, changing colors, etc.—of the status of a cleaning or calibration cycle, a sensor fault or upset condition (e.g. exceedance of probe slope), and the like.

Some embodiments of the present invention may limit the exposure of users and technicians to potentially hazardous cleaning and calibration chemicals by providing an internal chemical manifold within a sensor holder assembly block. In embodiments, the manifold may, by chemically resistant quick-disconnect valves, interconnect and/or be in fluid communication with a vent-free, collapsible storage container, and stopcock shutoff valves may be provided at one or more inlets to the manifold to allow for manual introduction of cleaning and calibration chemicals. Additionally and/or alternatively, the devices and systems of the invention may incorporate needle or bullet valves into the plastic block of the sensor holder assembly.

In one aspect of the present invention, a sensor cleaning and calibration system comprises a sensor holder assembly, comprising a block of solid plastic material, configured to receive and securely hold a sensor electrode by a mechanical interconnection, wherein the sensor electrode comprises an electrode tip and is configured to measure a parameter of a stream of an aqueous analyte, wherein the block of solid plastic material surrounds and defines an electrode column, the electrode column being configured to house the electrode tip of the sensor electrode; an analyte inlet for receiving the aqueous analyte stream; an analyte outlet for discharging the aqueous analyte stream; a check valve associated with the analyte inlet, configured to prevent backflow of the aqueous analyte stream; a main drain assembly, comprising a first drain valve, wherein the first drain valve is reconfigurable between an actuated configuration and a non-actuated configuration, wherein the first drain valve allows the aqueous analyte stream to flow into the electrode column when in the non-actuated configuration and drains the aqueous analyte stream away from the electrode column when in the actuated configuration; a secondary drain assembly, comprising a second drain valve, wherein the second drain valve is reconfigurable between an actuated configuration and a non-actuated configuration, wherein the second drain valve allows aqueous analyte to be retained in the electrode column and at least partially surround the electrode tip when in the non-actuated configuration and drains the electrode column of aqueous analyte when in the actuated configuration; a cleaning or calibration fluid inlet, adapted to receive a cleaning or calibration fluid; and a spray/fill diffuser, operable to spray or flow the received cleaning or calibration fluid into the electrode column to clean or calibrate the sensor electrode or a portion thereof.

In embodiments, the mechanical interconnection may comprise a threaded or socket connection.

In embodiments, the system may further comprise a visual inspection device, mounted on or within the sensor holder assembly and positioned to enable a user to visually inspect the electrode tip. The visual inspection device may, but need not, comprise one or more selected from the group consisting of a magnifying lens, at least one light-emitting diode (LED), and a remotely operable camera.

In embodiments, the system may further comprise means for receiving a stream of fresh or potable water, wherein the spray/fill diffuser is operable to spray or rinse the sensor electrode or a portion thereof with the received fresh or potable water. The system may, but need not, further comprise a heater for heating the received clean water prior to spraying or rinsing the sensor electrode or a portion thereof. The heater may, but need not, comprise a point-of-use water heater.

In embodiments, the system may further comprise a manual fluid injection port, comprising a lock fitting and a manual valve, configured to receive and dispense into the electrode column a manually administered aliquot of the cleaning or calibration fluid.

In embodiments, the system may further comprise an ultrasonic transducer disposed proximal to the electrode tip and configured to provide an ultrasonic cleaning function to the sensor electrode.

In embodiments, the parameter may be selected from the group consisting of pH, dissolved oxygen content, ammonia content, chlorine content, monochloramine content, ozone content, total suspended solid content, mixed liquor suspended solid content, and ultraviolet transmittance. These parameters are merely non-limiting examples, and sensors measuring additional or alternative parameters are within the scope of the present invention.

In embodiments, the system may further comprise a non-transitory computer-readable medium storing instructions that, when executed by a computer processor, cause the computer processor to initiate a cleaning or calibration procedure by performing the steps of actuating the first drain valve; actuating the second drain valve; and activating the spray/fill diffuser.

In another aspect of the present invention, a sensor cleaning and calibration system comprises a sensor holder assembly, comprising a block of solid plastic material, configured to receive and securely hold each of at least first and second sensor electrodes by a mechanical interconnection, wherein each of the first and second sensor electrodes comprises an electrode tip and is configured to measure a parameter of a stream of an aqueous analyte, wherein the block of solid plastic material surrounds and defines at least first and second electrode columns, the first electrode column being configured to house the electrode tip of the first sensor electrode and the second electrode column being configured to house the electrode tip of the second sensor electrode; at least one analyte inlet for receiving the aqueous analyte stream; at least one analyte outlet for discharging the aqueous analyte stream; a check valve associated with the analyte inlet, configured to prevent backflow of the aqueous analyte stream; a main drain assembly, comprising a first drain valve, wherein the first drain valve is reconfigurable between an actuated configuration and a non-actuated configuration, wherein the first drain valve allows the aqueous analyte stream to flow into at least one selected electrode column when in the non-actuated configuration and drains the aqueous analyte stream away from the at least one selected electrode column when in the actuated configuration; a secondary drain assembly, comprising a second drain valve, wherein the second drain valve is reconfigurable between an actuated configuration and a non-actuated configuration, wherein the second drain valve allows aqueous analyte to be retained in the at least one selected electrode column and at least partially surround the electrode tips within the at least one selected electrode column when in the non-actuated configuration and drains the at least one selected electrode column of aqueous analyte when in the actuated configuration; at least one cleaning or calibration fluid inlet, adapted to receive a cleaning or calibration fluid; a first spray/fill diffuser associated with the first electrode column, operable to spray or flow received cleaning or calibration fluid into the first electrode column to clean or calibrate the first sensor electrode or a portion thereof; and a second spray/fill diffuser associated with and the second electrode column, operable to spray or flow received cleaning or calibration fluid into the second electrode column to clean or calibrate the second sensor electrode or a portion thereof.

In embodiments, the at least one analyte inlet may consist of a single analyte inlet and the at least one analyte outlet consists of a single analyte outlet, the single analyte inlet may direct portions of the aqueous analyte stream into both the first and second electrode columns, and the single analyte outlet may discharge the aqueous analyte stream from both the first and second electrode columns.

In embodiments, the at least one cleaning or calibration fluid inlet may consist of a single cleaning or calibration fluid inlet.

In embodiments, the at least one selected electrode column may comprise both the first and second electrode columns.

In embodiments, the parameter may be selected from the group consisting of pH, dissolved oxygen content, ammonia content, chlorine content, monochloramine content, ozone content, total suspended solid content, mixed liquor suspended solid content, and ultraviolet transmittance. These parameters are merely non-limiting examples, and sensors measuring additional or alternative parameters are within the scope of the present invention.

In embodiments, the system may further comprise a non-transitory computer-readable medium storing instructions that, when executed by a computer processor, cause the computer processor to initiate a cleaning or calibration procedure by performing the steps of actuating the first drain valve; actuating the second drain valve; and activating at least one of the first spray/fill diffuser and the second spray/fill diffuser.

In another aspect of the present invention, a sensor cleaning and calibration system comprises a sensor holder assembly, comprising a block of solid plastic material, configured to receive and securely hold a sensor electrode by a mechanical interconnection, wherein the sensor electrode comprises an electrode tip and is configured to measure a parameter of an aqueous analyte, wherein the block of solid plastic material surrounds and defines an electrode column, wherein the electrode column is configured to house the electrode tip; an analyte inlet for receiving the aqueous analyte; an analyte outlet for discharging the aqueous analyte; a check valve associated with the analyte inlet, configured to prevent backflow of the aqueous analyte stream; a main drain assembly, comprising a first drain valve, wherein the first drain valve is reconfigurable between an actuated configuration and a non-actuated configuration, wherein the first drain valve allows the aqueous analyte to flow into the electrode column when in the non-actuated configuration and drains the aqueous analyte away from the electrode column when in the actuated configuration; a secondary drain assembly, comprising a second drain valve, wherein the second drain valve is reconfigurable between an actuated configuration and a non-actuated configuration, wherein the second drain valve allows aqueous analyte to be retained in the electrode column and at least partially surround the electrode tip when in the non-actuated configuration and drains the electrode column of aqueous analyte when in the actuated configuration; a cleaning or calibration fluid inlet, adapted to receive a cleaning or calibration fluid; a spray/fill diffuser, operable to spray or flow the received cleaning or calibration fluid into the electrode column to clean or calibrate the sensor electrode or a portion thereof; and a non-transitory computer-readable medium storing instructions that, when executed by a computer processor, cause the computer processor to perform a method comprising at least one of (i) allowing aqueous analyte to flow from a first region within an analyte vessel into the analyte inlet by opening, or maintaining as open, a solenoid valve associated with a first sample line and closing, or maintaining as closed, a solenoid valve associated with a second sample line; (ii) allowing aqueous analyte to flow from a second region within the analyte vessel into the analyte inlet by closing, or maintaining as closed, the solenoid valve associated with the first sample line and opening, or maintaining as open, the solenoid valve associated with the second sample line; (iii) allowing aqueous analyte to flow from both the first and second regions into the analyte inlet by opening, or maintaining as open, the solenoid valves associated with both the first and second sample lines; and (iv) preventing aqueous analyte from flowing from either the first or second region into the analyte inlet by closing, or maintaining as closed, the solenoid valves associated with both the first and second sample lines, wherein the first and second sample lines are both in fluid communication with the analyte inlet, the first sample line is configured to withdraw aqueous analyte from the first region of the analyte vessel, and the second sample line is configured to withdraw aqueous analyte from the second region of the analyte vessel.

In embodiments, the parameter may be selected from the group consisting of pH, dissolved oxygen content, ammonia content, chlorine content, monochloramine content, ozone content, total suspended solid content, mixed liquor suspended solid content, and ultraviolet transmittance. These parameters are merely non-limiting examples, and sensors measuring additional or alternative parameters are within the scope of the present invention.

In another aspect of the present invention, a sensor cleaning and calibration system comprises a sensor holder assembly, comprising a block of solid plastic material, configured to receive and securely hold a sensor electrode by a mechanical interconnection, wherein the sensor electrode comprises an electrode tip and is configured to measure a parameter of an aqueous analyte, wherein the block of solid plastic material surrounds and defines an electrode column, the electrode column being configured to house the electrode tip and having at least one sidewall; a column isolation assembly, comprising a column isolation valve, wherein the column isolation valve is reconfigurable between an actuated configuration and a non-actuated configuration, wherein the column isolation valve allows the aqueous analyte stream to flow into the electrode column when in the non-actuated configuration and directs the aqueous analyte stream away from the electrode column when in the actuated configuration; a drain assembly, comprising a drain valve, wherein the drain valve is reconfigurable between an actuated configuration and a non-actuated configuration, wherein the drain valve allows aqueous analyte to be retained in the electrode column and at least partially surround the electrode tip when in the non-actuated configuration and drains the electrode column of aqueous analyte when in the actuated configuration; at least one fluid injection port, each fluid injection port comprising a selectively reconfigurable valve; an internal chemical manifold, in fluid communication with the at least one fluid injection port; and upper, central, and lower spray diffusers, configured to receive fluid from the internal chemical manifold and spray fluid within the electrode column, wherein a spray pattern of the central spray diffuser is narrower than a spray pattern of at least one of the upper spray diffuser and the lower spray diffuser, wherein the upper and lower spray diffusers are configured to spray fluid on at least a portion of the at least one sidewall of the electrode column and the central spray diffuser is configured to spray fluid on at least a portion of the electrode tip, and wherein diffuser surfaces of the upper, central, and lower spray diffusers are substantially flush with the at least one sidewall of the electrode column.

In embodiments, the mechanical interconnection may comprise a threaded or socket connection.

In embodiments, the system may further comprise a visual inspection device, mounted on or within the sensor holder assembly and positioned to enable a user to visually inspect the electrode tip. The visual inspection device may, but need not, comprise one or more selected from the group consisting of a magnifying lens, at least one light-emitting diode (LED), and a remotely operable camera. The visual inspection device may, but need not, be a magnifying lens having 4× magnification and positioned at a distance of between about 0.8 inches and about 1.0 inch from a center of the electrode tip. The visual inspection device and the electrode tip may, but need not, be disposed at an angle relative to each other.

In embodiments, the selectively reconfigurable valve may be selected from the group consisting of a stopcock valve and a bullet/stem type needle valve.

In embodiments, a diameter of the spray pattern of the central spray diffuser may be between about 90% and about 120% of a diameter of the electrode tip.

In embodiments, at least a portion of an outer surface of at least one of the upper spray diffuser, the central spray diffuser, and the lower spray diffuser may be constructed of polytetrafluoroethylene.

In embodiments, the system may further comprise a light-emitting diode configured to provide a visual indicator of an operating condition of the system. The operating condition may, but need not, be selected from the group consisting of an in-progress cleaning procedure, an in-progress calibration procedure, and a sensor fault condition.

In embodiments, the sensor electrode may comprise an electrode cap. The electrode cap may, but need not, be substantially flush with a portion of the at least one sidewall of the electrode column. The electrode cap may, but need not, be at least partially constructed from polytetrafluoroethylene.

In embodiments, the parameter may be selected from the group consisting of pH, dissolved oxygen content, ammonia content, chlorine content, monochloramine content, ozone content, total suspended solid content, mixed liquor suspended solid content, and ultraviolet transmittance. These parameters are merely non-limiting examples, and sensors measuring additional or alternative parameters are within the scope of the present invention.

In embodiments, the system may further comprise a non-transitory computer-readable medium storing instructions that, when executed by a computer processor, cause the computer processor to initiate a cleaning or calibration procedure by performing the steps of actuating the column isolation valve; actuating the drain valve; and activating at least one of the upper spray diffuser, the central spray diffuser, and the lower spray diffuser.

In another aspect of the present invention, a method for cleaning or calibrating a sensor comprises (a) actuating a valve of a main drain assembly to redirect flow of a stream of an aqueous analyte away from an electrode column of a sensor holder assembly, wherein an electrode tip of the sensor is disposed within the electrode column; (b) actuating a valve of a secondary drain assembly to drain residual aqueous analyte out of the electrode column; and (c) dispensing a cleaning or calibration fluid within the electrode column to cause at least a portion of the cleaning or calibration fluid to contact the sensor electrode.

In embodiments, steps (a) and (b) may be carried out simultaneously.

In embodiments, the method may further comprise (d) returning the valves of the main drain assembly and the secondary drain assembly to a non-actuated state to cause the aqueous analyte stream to flow into the electrode column and at least partially surround the electrode tip of the sensor.

These and other advantages will be apparent from the disclosure of the aspects, embodiments, and configurations contained herein.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "means" as used herein shall be given its broadest possible interpretation in accordance with 35 U.S.C., Section 112(f) and/or Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the disclosure, brief description of the drawings, detailed description, abstract, and claims themselves.

Unless otherwise noted, all component or composition levels are in reference to the active portion of that component or composition and are exclusive of impurities, for example, residual solvents or by-products, which may be present in commercially available sources of such components or compositions.

All percentages and ratios are calculated by total composition weight, unless indicated otherwise.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein. By way of example, the phrase from about 2 to about 4 includes the whole number and/or integer ranges from about 2 to about 3, from about 3 to about 4 and each possible range based on real (e.g., irrational and/or rational) numbers, such as from about 2.1 to about 4.9, from about 2.1 to about 3.4, and so on.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

Figure 1:
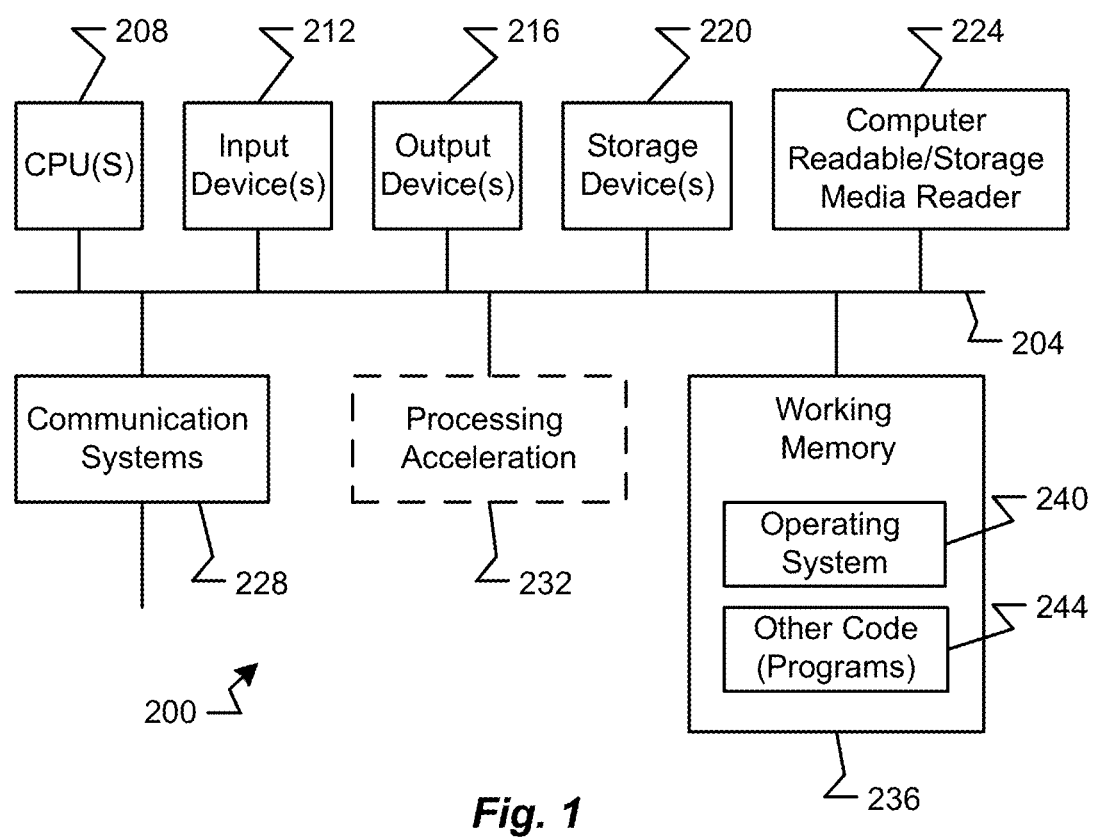
FIG. 1 is a block diagram illustrating elements of an exemplary computing device in which embodiments of the present disclosure may be implemented.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

DETAILED DESCRIPTION OF THE INVENTION

In the following description, for the purposes of explanation, numerous specific details are set forth in order to provide a thorough understanding of various embodiments disclosed herein. It will be apparent, however, to one skilled in the art that various embodiments of the present disclosure may be practiced without some of these specific details. The ensuing description provides exemplary embodiments only, and is not intended to limit the scope or applicability of the disclosure. Furthermore, to avoid unnecessarily obscuring the present disclosure, the preceding description omits a number of known structures and devices. This omission is not to be construed as a limitation of the scopes of the claims. Rather, the ensuing description of the exemplary embodiments will provide those skilled in the art with an enabling description for implementing an exemplary embodiment. It should however be appreciated that the present disclosure may be practiced in a variety of ways beyond the specific detail set forth herein.

While the exemplary aspects, embodiments, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices or collocated on a particular node of a distributed network, such as an analog and/or digital telecommunications network, a packet-switch network, or a circuit-switched network. It will be appreciated from the following description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

As used herein, the phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising," "including," and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

A "computer readable signal" medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable medium may be transmitted using any appropriate medium, including but not limited to wireless, wireline, optical fiber cable, RF, etc., or any suitable combination of the foregoing.

The terms "determine," "calculate," and "compute," and variations thereof, as used herein, are used interchangeably and include any type of methodology, process, mathematical operation or technique.

It shall be understood that the term "means" as used herein shall be given its broadest possible interpretation in accordance with 35 U.S.C. § 112(f). Accordingly, a claim incorporating the term "means" shall cover all structures, materials, or acts set forth herein, and all of the equivalents thereof. Further, the structures, materials or acts and the equivalents thereof shall include all those described in the summary of the disclosure, brief description of the drawings, detailed description, abstract, and claims themselves.

Aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Any combination of one or more computer readable medium(s) may be utilized. The computer readable medium may be a computer readable signal medium or a computer readable storage medium.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations, and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

Examples of the processors as described herein may include, but are not limited to, at least one of Qualcomm® Snapdragon® 800 and 801, Qualcomm® Snapdragon® 610 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARM926EJ-S™ processors, other industry-equivalent processors, and may perform computational functions using any known or future-developed standard, instruction set, libraries, and/or architecture.

In yet another embodiment, the disclosed methods may be readily implemented in conjunction with software using object or object-oriented software development environments that provide portable source code that can be used on a variety of computer or workstation platforms. In additional embodiments, the disclosed methods may be implemented in conjunction with functional programming. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein, and other similar standards and protocols not mentioned herein are periodically superseded by faster or more effective equivalents having essentially the same functions. Such replacement standards and protocols having the same functions are considered equivalents included in the present disclosure.

FIG. 1 is a block diagram illustrating elements of an exemplary computing device in which embodiments of the present disclosure may be implemented. More specifically, this example illustrates one embodiment of a computer system 200 upon which the servers, user computers, computing devices, or other systems or components described above may be deployed or executed. The computer system 200 is shown comprising hardware elements that may be electrically coupled via a bus 204. The hardware elements may include one or more Central Processing Units (CPUs) 208; one or more input devices 212 (e.g., a mouse, a keyboard, etc.); and one or more output devices 216 (e.g., a display device, a printer, etc.). The computer system 200 may also include one or more storage devices 220. By way of example, storage device(s) 220 may be disk drives, optical storage devices, solid-state storage devices such as a Random-Access Memory (RAM) and/or a Read-Only Memory (ROM), which can be programmable, flash-updateable and/or the like.

The computer system 200 may additionally include a computer-readable storage media reader 224; a communications system 228 (e.g., a modem, a network card (wireless or wired), an infra-red communication device, etc.); and working memory 236, which may include RAM and ROM devices as described above. The computer system 200 may also include a processing acceleration unit 232, which can include a Digital Signal Processor (DSP), a special-purpose processor, and/or the like.

The computer-readable storage media reader 224 can further be connected to a computer-readable storage medium, together (and, optionally, in combination with storage device(s) 220) comprehensively representing remote, local, fixed, and/or removable storage devices plus storage media for temporarily and/or more permanently containing computer-readable information. The communications system 228 may permit data to be exchanged with a network and/or any other computer described above with respect to the computer environments described herein. Moreover, as disclosed herein, the term "storage medium" may represent one or more devices for storing data, including ROM, RAM, magnetic RAM, core memory, magnetic disk storage mediums, optical storage mediums, flash memory devices and/or other machine-readable mediums for storing information.

The computer system 200 may also comprise software elements, shown as being currently located within a working memory 236, including an operating system 240 and/or other code 244. It should be appreciated that alternate embodiments of a computer system 200 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 208 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARIV1926EJ-S™ processors, other industry-equivalent processors, and may perform computational functions using any known or future-developed standard, instruction set, libraries, and/or architecture.

Figure 2:
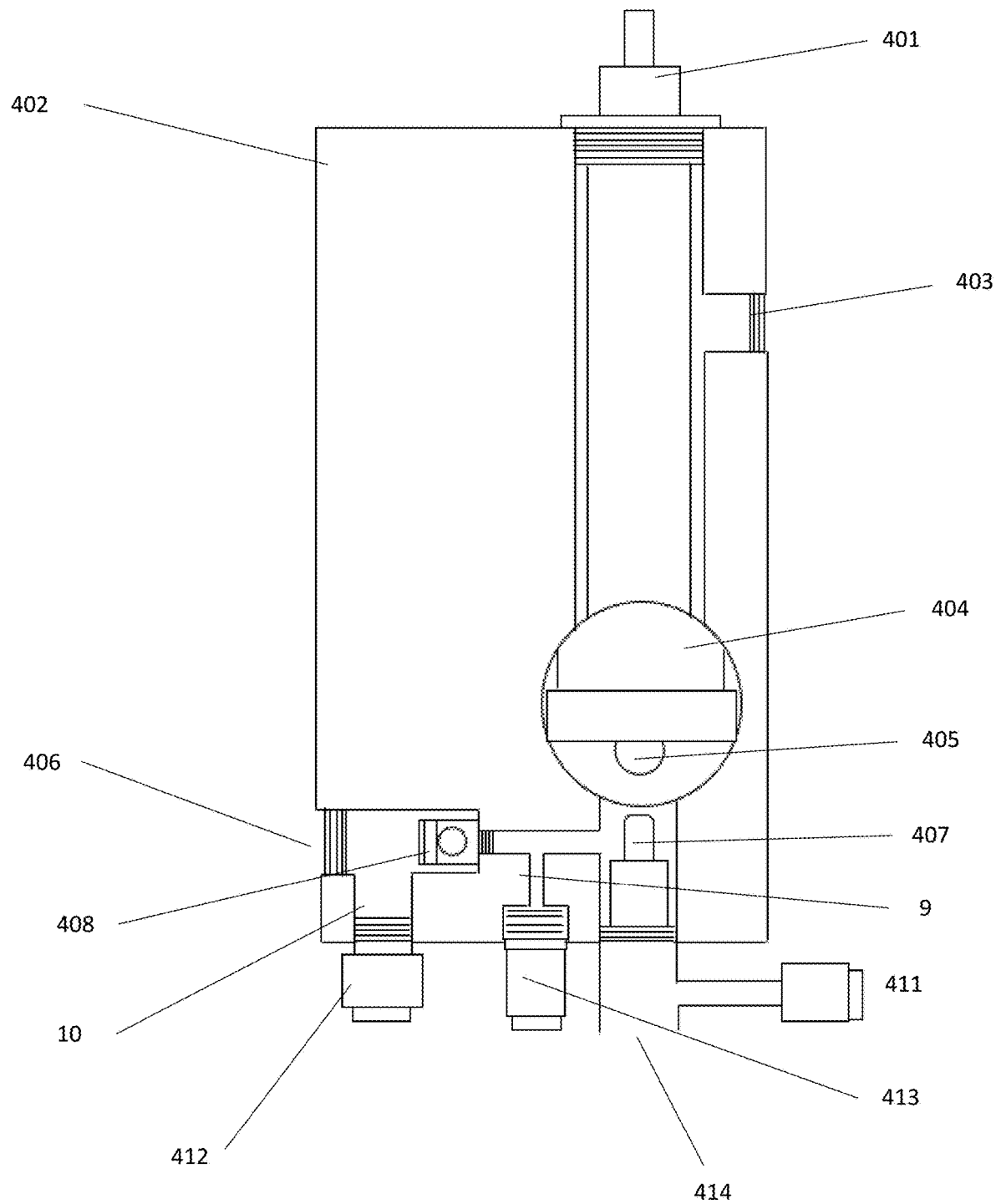
FIG. 2 is a perspective view of a sensor holder assembly for a single pH sensor having a side inlet configuration, according to embodiments of the present invention.

Referring now to FIG. 2, various elements of a cleaning and calibration assembly (a "device") for a sensor 401, in this case a pH sensor, are illustrated. The pH sensor 401, which includes an electrode tip 405, is securely received and held by a mechanical interconnection, e.g. a threaded or socket connection, of an assembly block 402. In the embodiment illustrated in FIG. 2, the assembly block 402 includes or operates in conjunction with various other components, such as a fluid discharge outlet 403, a magnifying lens 404, a fluid inlet 406, a spray/fill diffuser 407, an inlet check valve 408, a fresh or potable water inlet assembly 411, a main drain assembly 412, a secondary drain assembly 413, and a chemical dosing inlet 414.

The assembly block 402 is generally machined from a single solid block of an acrylic or similar plastic material, i.e. a material with a high degree of structural integrity that is resistant to chemical and physical degradation (e.g. oxidation, acid degradation, water damage, etc.), and may be sized to accommodate any size of sensor 401 and/or electrode tip 405. Other similar materials besides acrylic may also be used. The assembly block 402 can be configured to receive and/or discharge any one or more fluids—an aqueous analyte stream, a stream of a cleaning or calibration fluid(s), a fresh or potable water stream, etc.—by either gravity-induced flow or pumped flow, and can operate at atmospheric pressure or greater than atmospheric pressure (e.g. by being in fluid communication with a pressurized line or tank). During normal sensor operations (i.e. when a cleaning or calibration procedure is not being performed), the main and secondary drain assemblies 412, 413 are not actuated, and an aqueous analyte stream—that is, a stream of the aqueous fluid intended to be measured or monitored by the sensor 401—can therefore enter the assembly block 402 via the fluid inlet 406, flow toward and at least partially surround or submerge the electrode tip 405, and exit the assembly block 402 via the fluid discharge outlet 403.

In the embodiment illustrated in FIG. 2, a magnifying lens 404 is provided proximal to the electrode tip 405 to allow a user or technician to visually inspect the electrode tip 405 (illustrated in FIG. 2 as magnified under the magnifying lens 404) without removing the sensor 401 or any portion thereof from the assembly block 402. The magnifying lens 404 may be press-fit or press-mounted within a routed or machined section of the assembly block 402. It is to be expressly understood that the magnifying lens 404 is only one of several visual inspection devices that may suitably be used in embodiments of the present invention, and that other visual inspection devices, such as LED lighting or a remotely operable camera, may be provided instead of or in addition the magnifying lens 404.

As illustrated in FIG. 2, most of the sensor 401, and in particular the electrode tip 405, is held within a void or space defined and surrounded by the assembly block 402; while this void or space is hereinafter referred to as the electrode "column," it is to be expressly understood that the sensor may, in embodiments, be mounted vertically, horizontally, or at any angle between a horizontal axis and a vertical axis. An advantage of the present invention lies in the ability to isolate the electrode column from flow of the aqueous analyte stream and drain any residual aqueous analyte out of the electrode column during a cleaning or calibration procedure, which may be accomplished by use of the inlet check valve 408, the main drain assembly 412, and the secondary drain assembly 413. The inlet check valve 408, which may be mounted internally (i.e. within the assembly block 402) or externally, prevents backflow of the aqueous analyte stream, and a cleaning or calibration cycle can be initiated by actuating a solenoid valve of the main drain assembly 412 to cause the aqueous analyte stream to be drained out of the assembly block 402 via the main drain assembly 412. In this way, the cleaning or calibration cycle can be initiated without the need to cease or shut off flow of the aqueous analyte stream to the assembly block 402, guaranteeing that the electrode tip 405 will receive a "fresh" analyte sample when the cleaning/calibration cycle is completed and the system is returned to normal measurement operations. Simultaneously with or subsequent to actuation of the solenoid valve of the main drain assembly 412, a solenoid valve of the secondary drain assembly 413 is actuated to cause any fluid (i.e. analyte) remaining in the electrode column to drain out of the assembly block 402 via the secondary drain assembly 413. With the electrode column now devoid of liquids that may hinder the cleaning or calibration process, appropriate cleaning or calibration fluids (e.g. acids, oxidants, surfactants, enzymes, buffers, etc.), injected into the assembly block 402 via the chemical dosing inlet 414, can be sprayed or rinsed into the electrode column and onto or about the electrode tip 405 via the spray/fill diffuser 407, at atmospheric or greater than atmospheric pressure.

In some embodiments, it may be advantageous to include a fresh or potable water inlet assembly 411. The fresh or potable water inlet assembly 411 interconnects to a source of fresh or potable water, such as a municipal water supply, and comprises a solenoid valve, which when actuated allows fresh or potable water to flow toward and be sprayed into the electrode column by the spray/fill diffuser 407. In this configuration, the electrode tip 405 may be sprayed, rinsed, or soaked with a stream of fresh or potable water as a first, last, or intermediate step of a cleaning or calibration process. In some embodiments, a backflow prevention device may be provided to prevent backflow of any residual analyte or cleaning or calibration chemical toward the fresh or potable water source. In further embodiments, the fresh or potable water inlet assembly 411 may be configured to provide water of a desired temperature, for example by including a point-of-use water heater that delivers heated fresh or potable water to the spray/fill diffuser 407.

Figure 3:
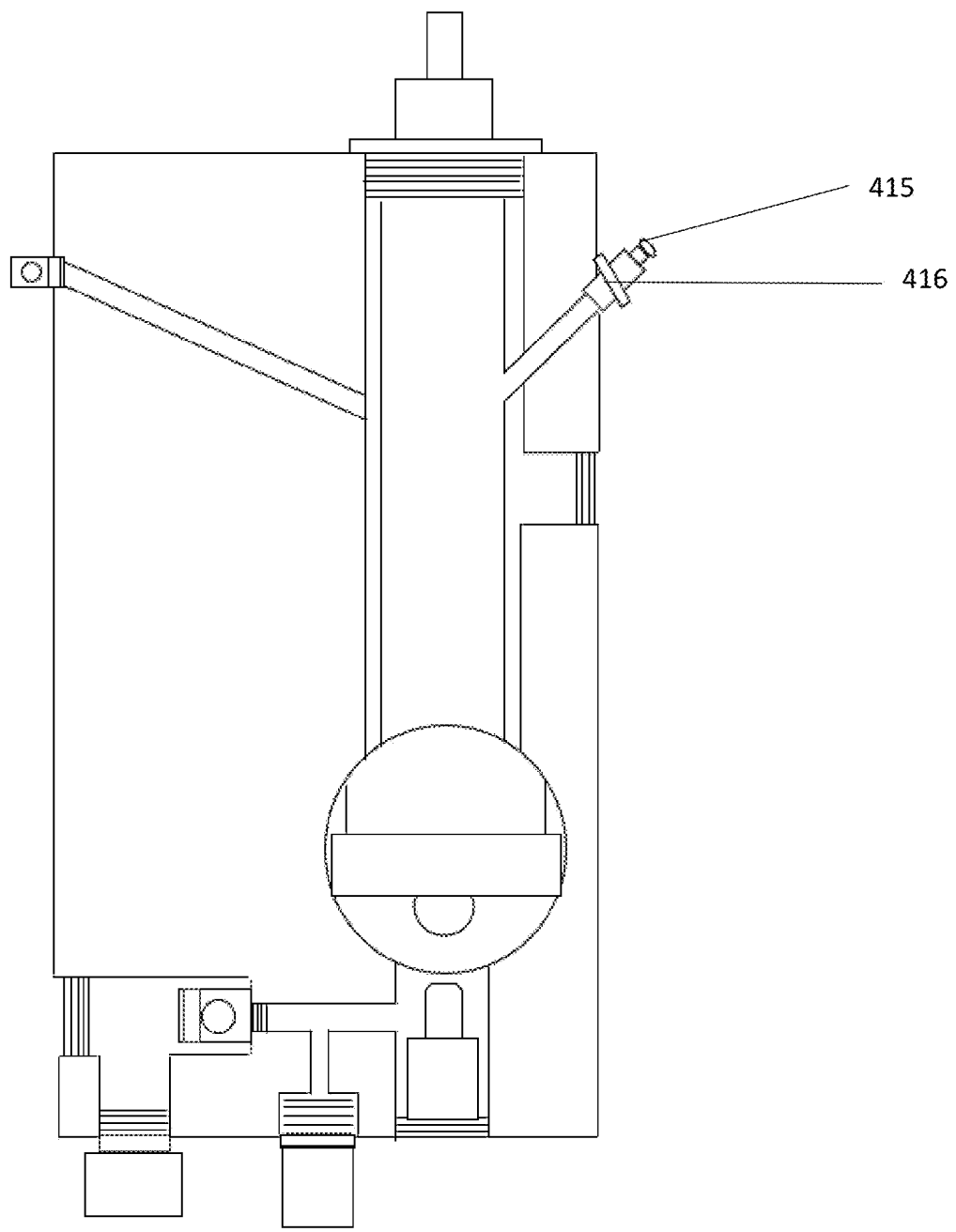
FIG. 3 is a perspective view of a sensor holder assembly for a single pH sensor having a side inlet configuration as part of a semi-automated cleaning and calibration system, according to embodiments of the present invention.

Referring now to FIG. 3, the device may be provided with a port that includes a Luer lock fitting (or other similar type of fitting) 415 and a manual valve 416. This configuration allows a user or technician to connect a syringe or similar fluid dosing device to the device via the Luer lock fitting 415, manually actuate the manual valve 416, and manually dose a cleaning or calibration chemical such as a buffer solution into the device. The features illustrated in FIG. 3 may be advantageous or beneficial for non-automated or semi-automated cleaning and calibration processes, which can thus benefit from the construction of the assembly block 402 and related components even without providing a programmable logic controller for automatic initiation and control of the cleaning and calibration steps. Such non-automated and semi-automated cleaning processes are thus within the scope of the present invention.

Figure 4:
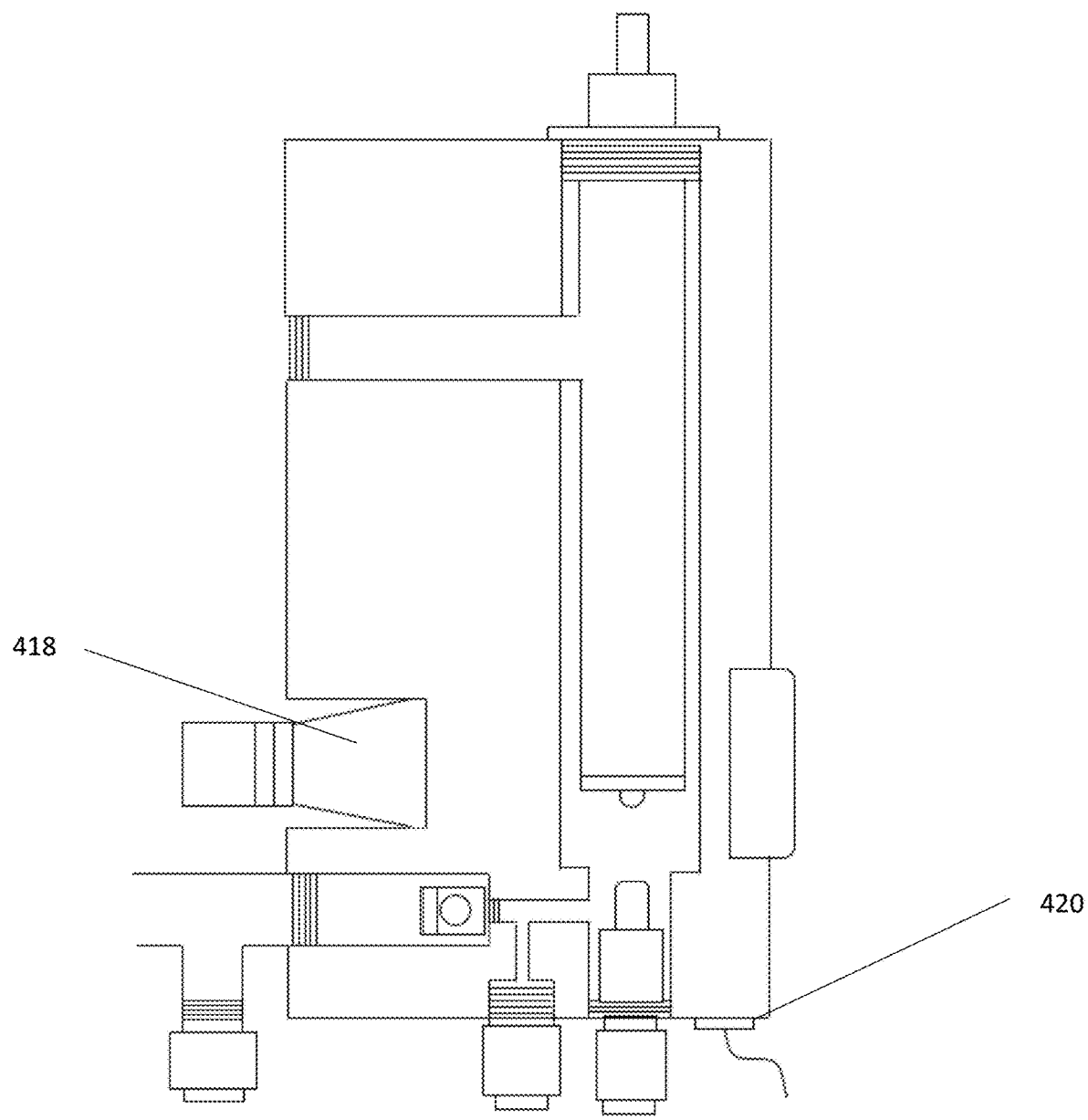
FIG. 4 is a perspective view of a sensor holder assembly for a single pH sensor having a rear inlet and rear outlet configuration, according to embodiments of the present invention.

Referring now to FIG. 4, embodiments of the device may be provided with an ultrasonic transducer 418 disposed proximal to, in this case opposite, the electrode tip 405. The transducer 418, like the magnifying lens 404 or other visual inspection device, can be press-mounted within a routed or machined section of the assembly block 402, at a depth that provides a desired pattern of vibration and/or oscillation when the ultrasonic transducer 418 is activated. The face of the ultrasonic transducer 418 can be exposed directly to the electrode column, or can be offset to allow sound waves to be conducted through the solid plastic material of the assembly block 402. This embodiment further includes an LED light 420 to illuminate the electrode tip.

Figure 5:
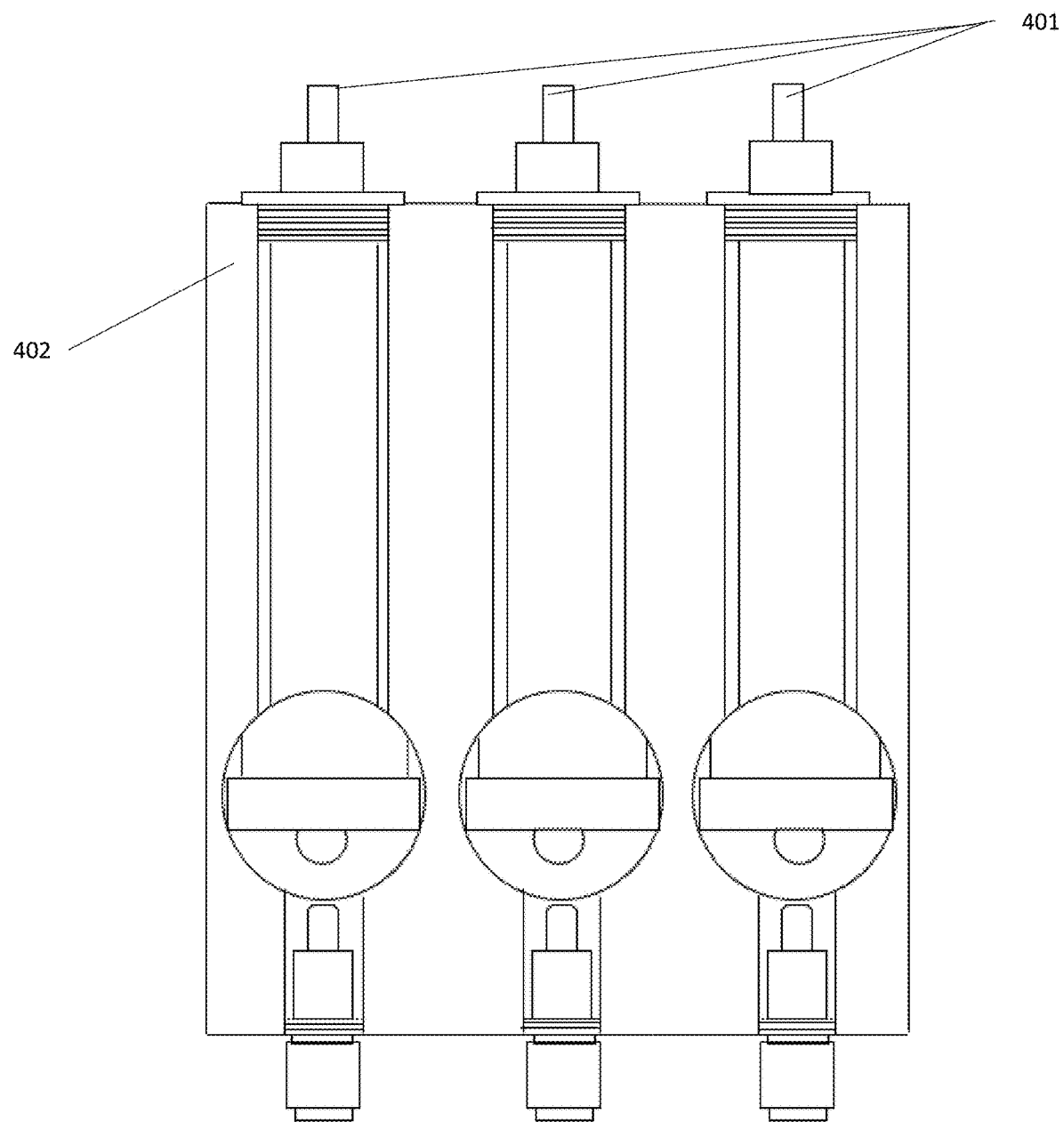
FIG. 5 is a perspective view of a sensor holder assembly for multiple pH sensors constructed from a single acrylic block, according to embodiments of the present invention.

Referring now to FIG. 5, an assembly block 402 may be provided that can accommodate multiple sensors 401, each such sensor being disposed within a separate one of several electrode columns of the assembly block 402. In the embodiment illustrated in FIG. 5, the other components of the device remain largely unchanged from the embodiment illustrated in FIG. 2 (and are thus not shown), with the exception that each electrode column may have a dedicated main drain assembly 412 and/or secondary drain assembly 413 to allow each electrode column to be isolated, and thus each sensor 401 cleaned or calibrated, independently of the other electrode columns and sensors 401.

Figure 6:
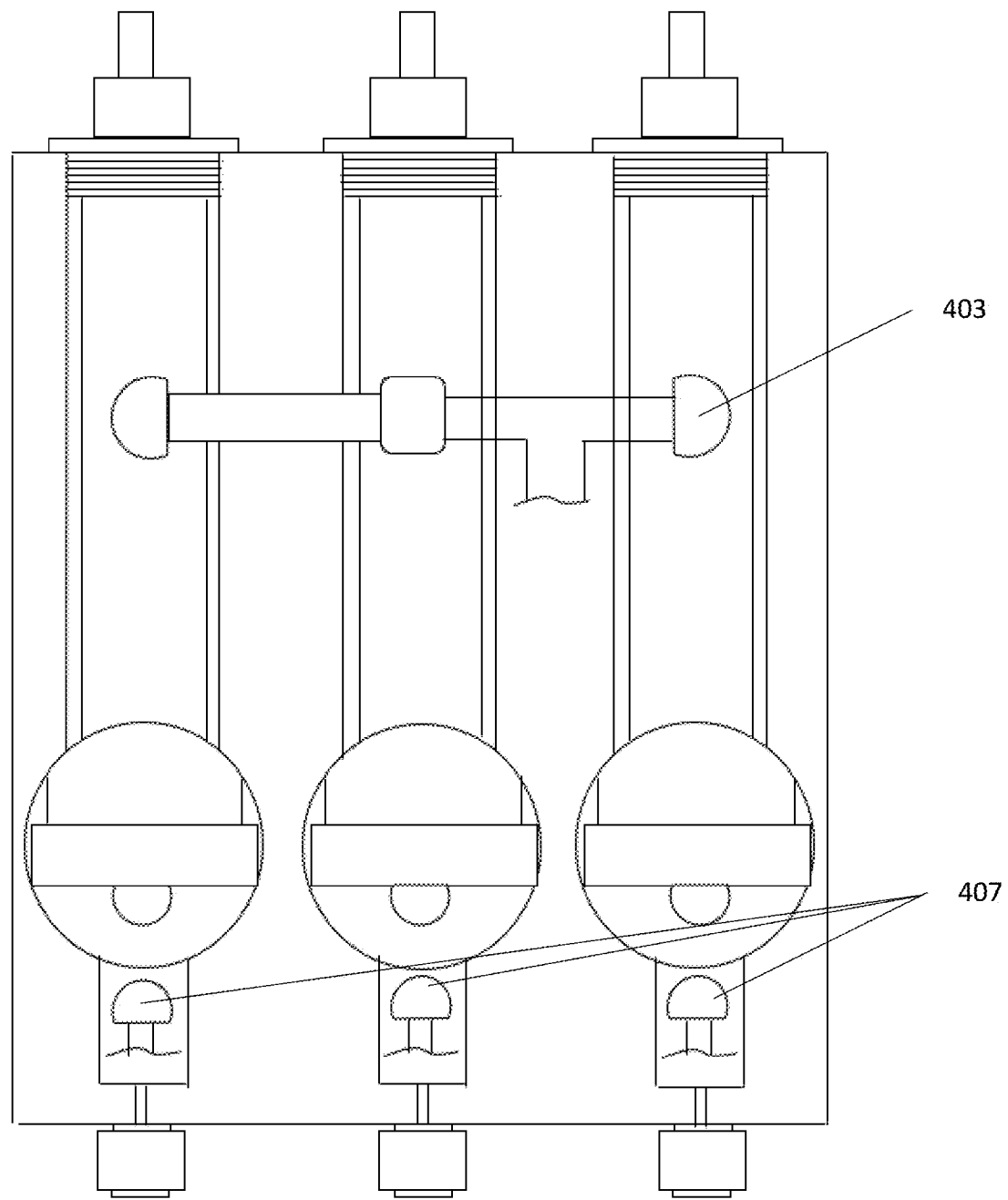
FIG. 6 is a perspective view of a sensor holder assembly for a single pH sensor having rear inlet and outlet connections, according to embodiments of the present invention.

Referring now to FIG. 6, another embodiment of a multi-sensor assembly block 402 is illustrated. In this embodiment, each of the several electrode columns may share a single fluid discharge outlet 403, while maintaining separate spray/fill diffusers 407.

Figure 7:
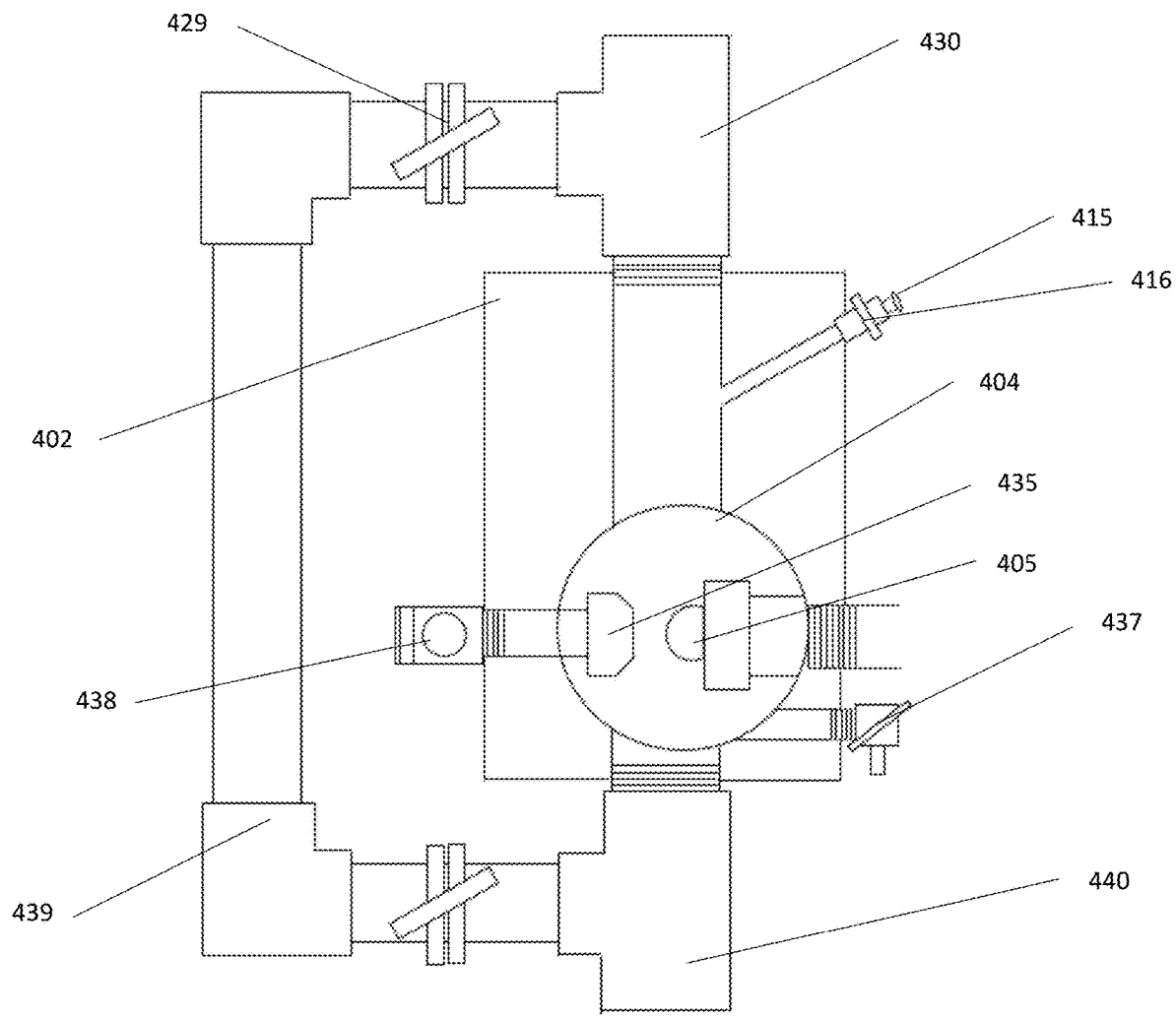
FIG. 7 is a perspective view of a sensor holder assembly having a single-flowthrough configuration with bypass and a manual dosing port as part of a semi-automated cleaning and calibration system, according to embodiments of the present invention.

Referring now to FIG. 7, an alternative design of a cleaning and calibration assembly is illustrated. The embodiment illustrated in FIG. 7 allows for in-line mounting of a sensor electrode that requires a side-entry installation. In this embodiment, the device can be installed and configured to work in conjunction with a "bypass" flow path of the aqueous analyte, e.g. as defined by flow path points 430, 439, 440, that can be manipulated to isolate the device from a "main" or "primary" flow stream of the analyte. Particularly, a manual valve 429 may be provided to allow a user or technician to selectively allow the analyte stream to flow through the device during normal operation, and to selectively prevent flow of the analyte stream through the device during cleaning or calibration; in the latter case, the user or technician can then remove any residual aqueous analyte remaining in the device via manual drain valve 437. Once the device has been drained of analyte, the user or technician may manually provide a cleaning or calibration fluid, e.g. from a syringe, via Luer lock or similar fitting 415 and manual valve 416, as described above with regard to the similar features illustrated in FIG. 3. In the embodiment illustrated in FIG. 7, a fresh or potable water inlet assembly, similar to the assembly 411 illustrated in FIG. 2, is provided with a manual valve, in this case interconnected to a check valve 438, which the user or technician may actuate to permit the flow of fresh or potable water into the device via a diffuser or similar element 435. As in the embodiment illustrated in FIG. 2, the embodiment illustrated in FIG. 7 is provided with a magnifying lens 404 (or other visual inspection device) to allow the user or technician to visually inspect the electrode tip 405 without removing the sensor 401 from the device. Additional or alternative features, such as those depicted in FIGS. 2-6, may be provided without departing from the scope of the invention.

Figure 8:
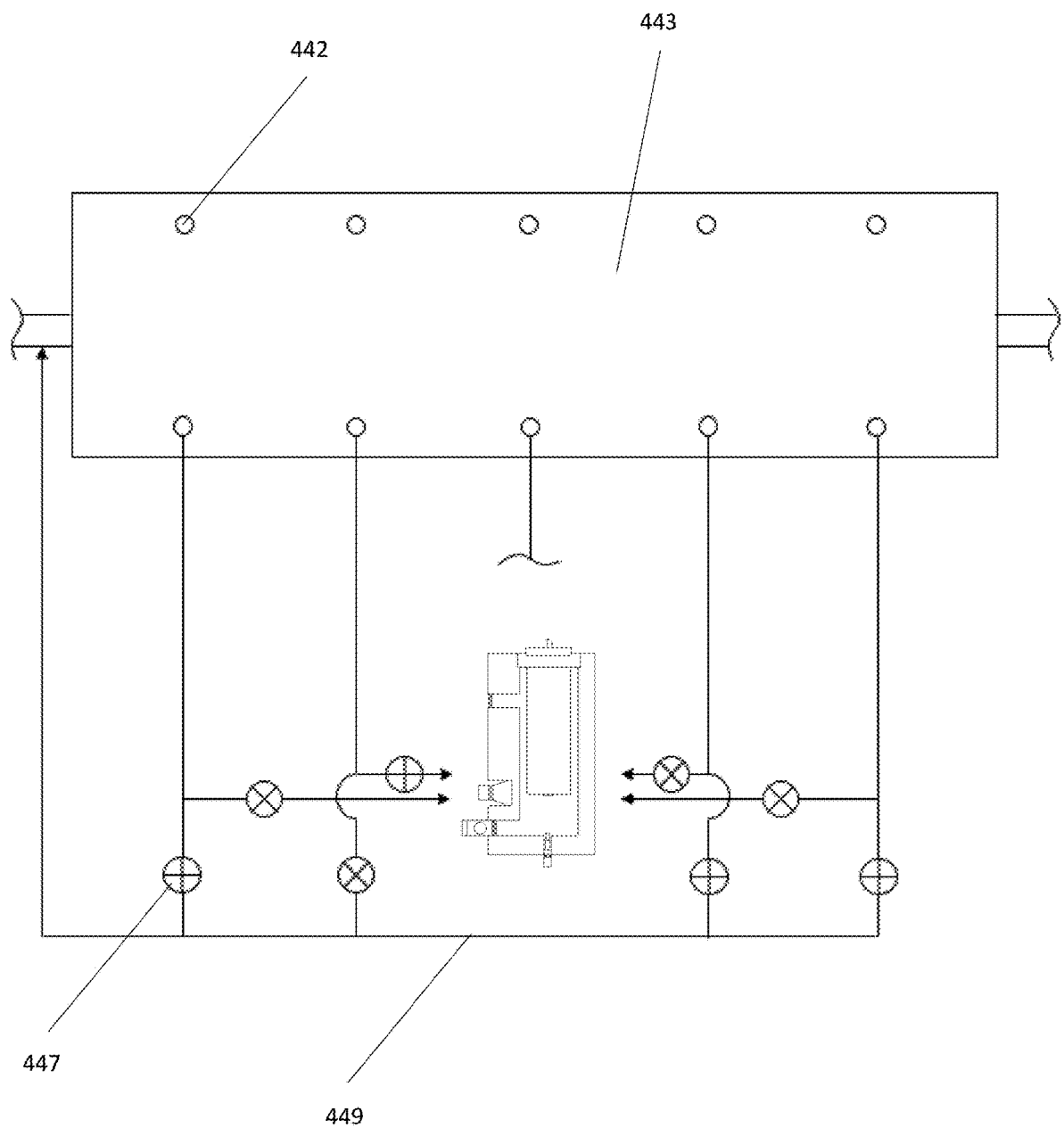
FIGS. 8 and 9 are perspective views of sensor holder assemblies for multiple dissolved oxygen or ammonia sensors for use in an alternating sampling process, according to embodiments of the present invention.

Referring now to FIG. 8, an embodiment of an automated cleaning and calibration system that can enable sampling of multiple regions within a volume of interest is illustrated. In this embodiment, a plurality of sample lines 442 penetrate the wall of an aeration basin or other analyte vessel 443 and interconnect to the sensor assembly block 402 via respective solenoid or motorized valves 447. By selective opening and closing of solenoid or motorized valves 447, aqueous analyte can be drawn into the device from individual zones within the aeration basin 443 and then discharged to a common return line (or drain) 449. In this way, the number of feed pumps and sensors needed to sample multiple regions of an aeration basin 443 can be reduced and/or the number of zones sampled by a single sensor can be increased, which may be particularly advantageous with regard to sensors that monitor conditions that may vary within the volume of interest (e.g. dissolved oxygen or ammonia content).

Figure 9:
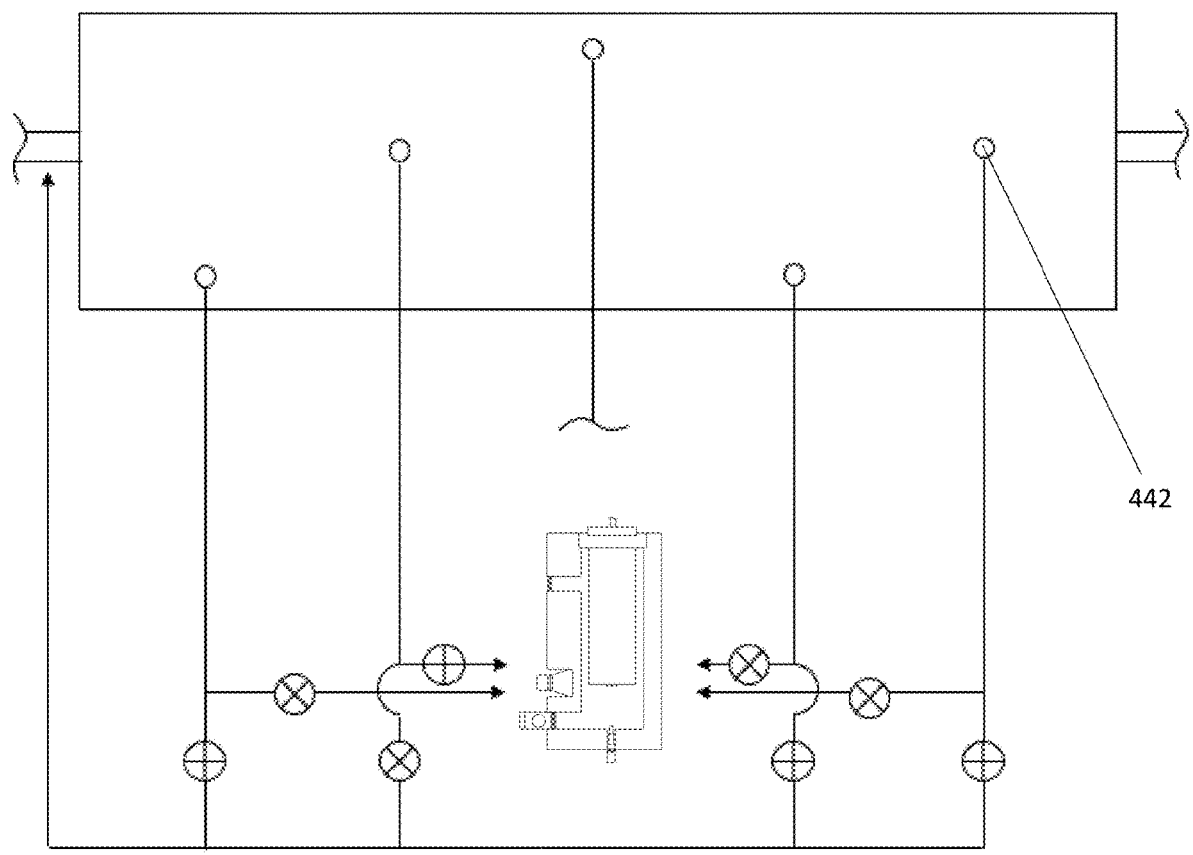

Referring now to FIG. 9, an alternative embodiment of an automated cleaning and calibration system that can enable sampling of multiple regions within a volume of interest is illustrated. Particularly, as illustrated in FIG. 9, sample lines 442 in the practice of the present invention may suitably withdraw aqueous analyte from a central portion of an aeration basin 443, in contrast to conventional systems (or the embodiment illustrated in FIG. 8) in which analyte is generally withdrawn only from the edges or periphery of the aeration basin 443.

Figure 10:
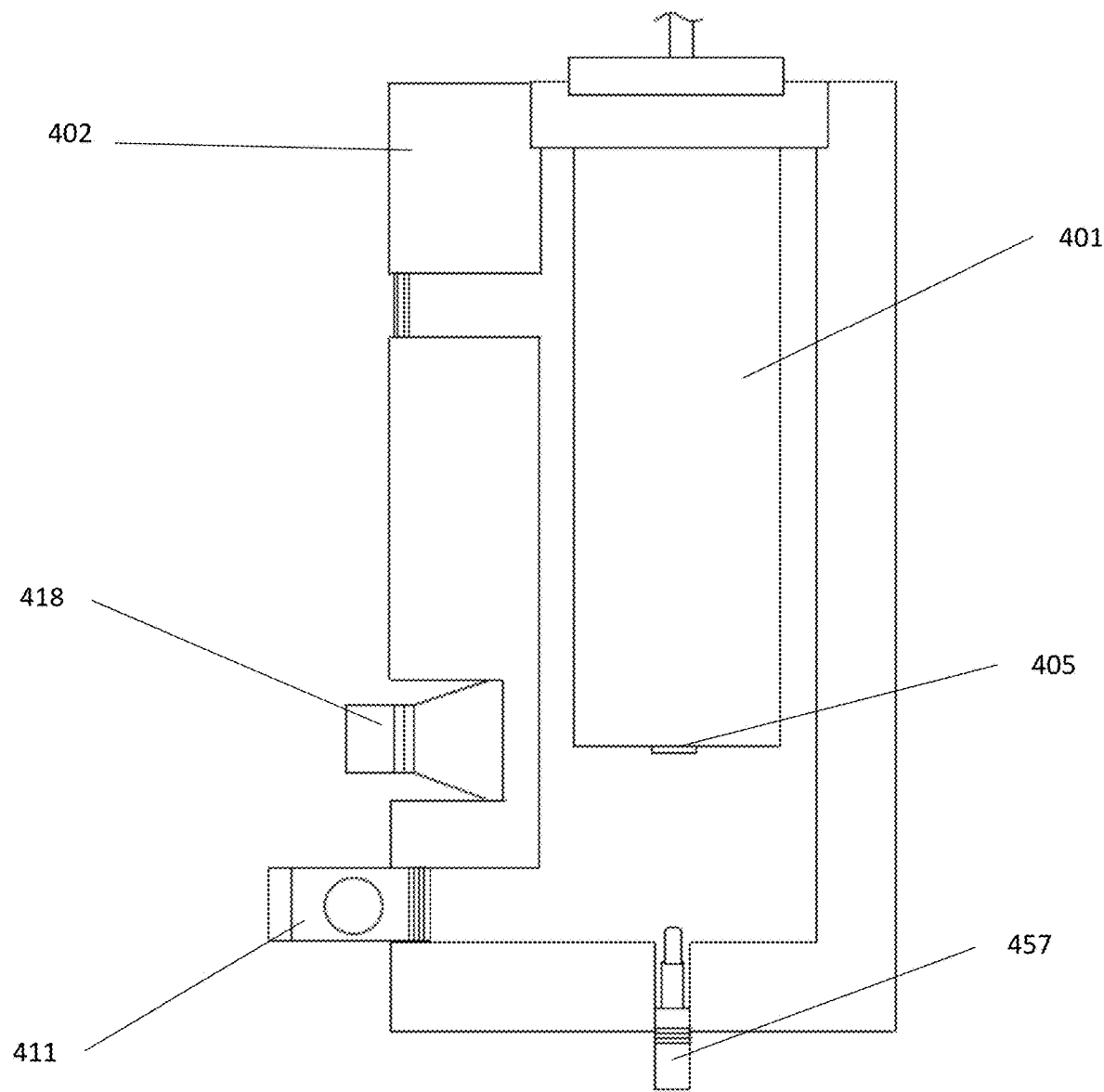
FIG. 10 is a perspective view of a sensor holder assembly for a single dissolved oxygen or other sensor having a rear inlet and outlet configuration, according to embodiments of the present invention.

Referring now to FIG. 10, devices and systems of the present invention may be provided with a rotating spray nozzle 457 instead of, or in addition to, a spray/fill diffuser 407 as illustrated in FIG. 2. A rotating spray nozzle may distribute a cleaning or calibration fluid over a wider area within the sensor column(s), which may be advantageous, for example, for cleaning or calibrating sensors having a large cross-sectional area of the electrode tip 405 (as illustrated in FIG. 10) or for using a single spray nozzle 457 to clean or calibrate multiple electrode tips 405 simultaneously or sequentially. Such embodiments, like the embodiments illustrated in other figures, may be suitable for any of a variety of sensors 401, including but not limited to pH sensors, dissolved oxygen sensors, ammonia sensors, total suspended solids sensors, ozone sensors, ultraviolet (UV) transmittance sensors, and combinations thereof. Embodiments including a rotating spray nozzle 457 may, as illustrated in FIG. 10, further incorporate elements shown in other figures, such as an ultrasonic transducer 418 and/or a solenoid valve-controlled fresh or potable water inlet assembly 411.

Figure 11A:
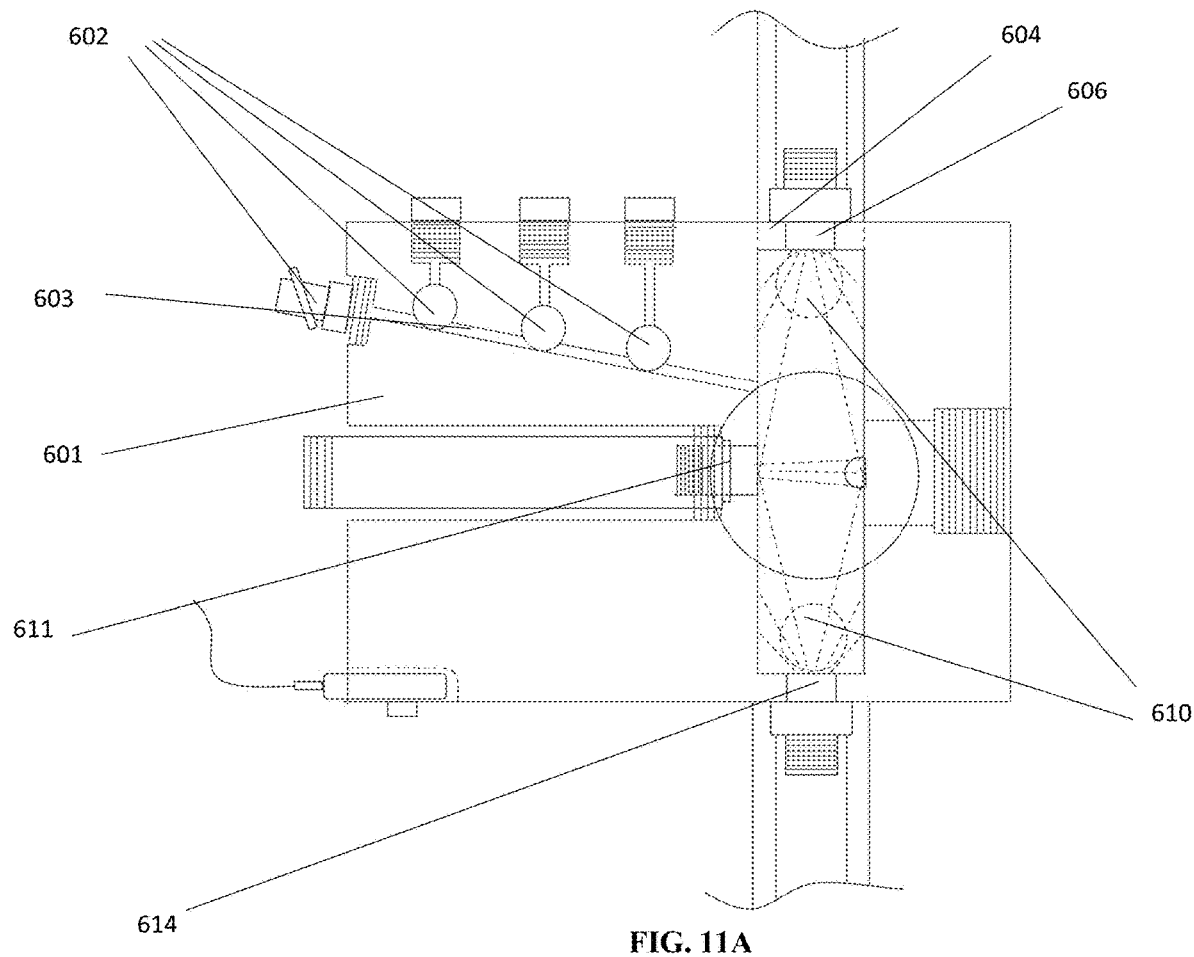
FIG. 11A is an illustration of an acrylic block sensor assembly, according to embodiments of the present invention.

Referring now to FIG. 11A, various elements of a cleaning and calibration assembly (a "device") for a sensor, in this case a pH sensor, are illustrated. The pH sensor, which includes an electrode tip, is securely received and held by a mechanical interconnection, e.g. a threaded or socket connection, of an assembly block 601. The assembly block 601 is generally machined from a single solid block of an acrylic or similar plastic material, i.e. a material with a high degree of structural integrity that is resistant to chemical and physical degradation (e.g. oxidation, acid degradation, water damage, etc.), and may be sized to accommodate any size of sensor and/or electrode tip. The assembly block 601 can be configured to receive and/or discharge any one or more fluids—an aqueous analyte stream, a stream of a cleaning or calibration fluid(s), a fresh or potable water stream, etc.—by either gravity-induced flow or pumped flow, and can operate at atmospheric pressure or greater than atmospheric pressure (e.g. by being in fluid communication with a pressurized line or tank).

In the embodiment illustrated in FIG. 11A, the assembly block 601 comprises or operates with a plurality of fluid injection ports 602 and an internal chemical manifold 603. The manifold 603 allows a plurality of different fluids to be injected into the assembly block 601 and thus applied to the sensor electrode in a desired fashion. Particularly, it may be desirable to introduce the most "aggressive," i.e. potentially damaging (corrosive, acidic, etc.), fluid via a fluid injection port closest to the electrode (thereby minimizing the length of the internal chemical manifold 603 exposed to the aggressive fluid), with less "aggressive" fluids successively introduced further from the electrode/toward a starting or entry point of the manifold. A "side" fluid injection port 602, i.e. a fluid injection port that introduces a fluid that travels the entire length of the internal chemical manifold 603, may in some cases be reserved for distilled or deionized water or similar fluid. It is to be expressly understood that there is no upper or lower limit on the number of fluid injection ports 602, and that devices including any number of fluid injection ports 602 may be provided within the scope of the present invention.

As illustrated in FIG. 11A, devices according to embodiments of the present invention may be provided with multiple spray diffusers or groups of spray diffusers; in this case, an upper spray diffuser 606, a central or electrode spray diffuser 611, and a lower spray diffuser 614 are provided. Each spray diffuser may be configured to provide a different spray pattern; particularly, upper and lower spray diffusers 606,614 may provide a wide spray pattern to clean sidewalls of the electrode column, whereas central spray diffuser 611 may provide a narrower spray pattern, in some cases to match, or only slightly exceed, an outer diameter of the sensor electrode to ensure full coverage of the sensor electrode with a cleaning or calibration fluid without wasting such fluid. In embodiments, a diameter of the spray pattern of the central spray diffuser 611 may be between about 90% and about 120% of a diameter of the electrode tip. The spray diffusers 606,611,614, or at least outer surfaces thereof, are preferably constructed of a chemically resistant, non-stick/low-friction material, such as polytetrafluoroethylene (PTFE, otherwise known as Teflon), and may be mounted within the assembly block 601 by a "press-fit" or similar mounting 604 that aligns the diffuser surface flush with the wall of the electrode column to prevent the accumulation of fluids or debris in a "gap" between the diffuser and the column. To accommodate the diffusers 606,611,614, other fluid inlet and outlet connections of the device (e.g. for receiving or discharging the aqueous analyte stream or fresh/potable water), such as fluid connections 610, may, relative to the embodiment illustrated in FIG. 2, be relocated to a rear aspect of the device.

Figure 11B:
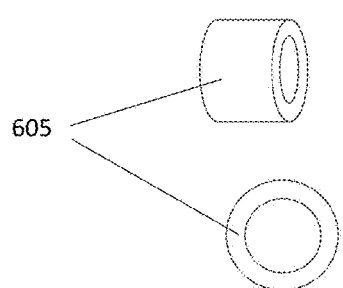
FIG. 11B is a perspective view of a press-fit ring of an acrylic block sensor assembly, according to embodiments of the present invention.

Referring now to FIG. 11B, a detail of the press-fit mounting 604 is illustrated. Particularly, the press-fit mounting comprises a press-fit "ring" 605 that is inserted into a space machined into a wall of the electrode column. The ring 605 is glued, cemented, or plastic-welded into place, thereby eliminating the gap between the surface of the diffuser and the wall of the electrode column.

Figure 12A:
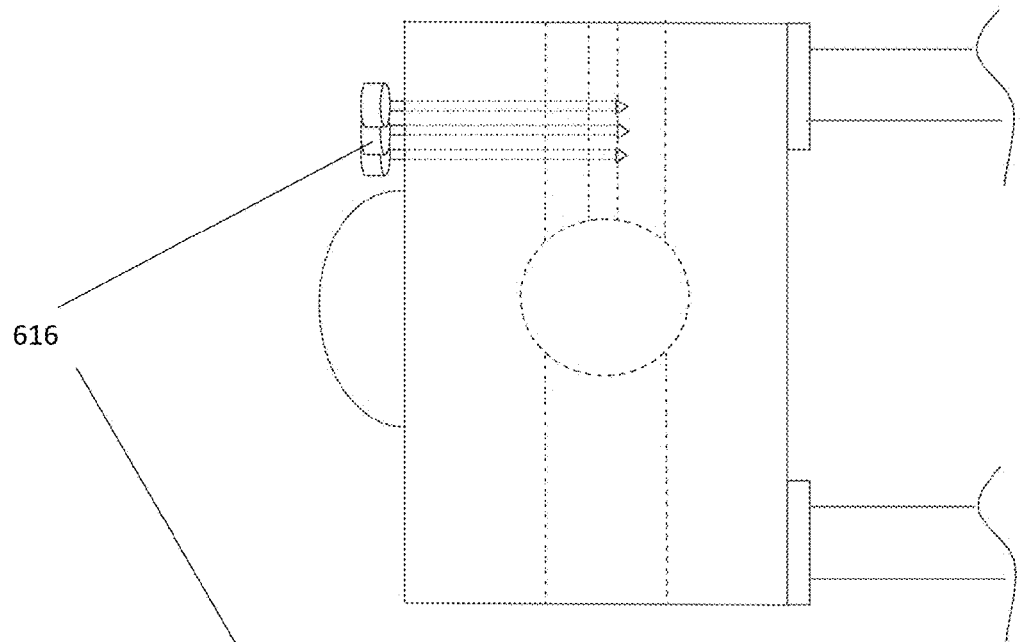
FIG. 12A is a perspective view of a sensor assembly utilizing "stem"-type needle or bullet valves, according to embodiments of the present invention.

Referring now to FIG. 12A, an embodiment of valves of an assembly block 601 is illustrated. In the embodiment illustrated in FIG. 12A, stem-type "bullet" valves 616 are provided, in addition to or instead of stopcock valves mounted on inlets of the fluid injection ports 602. The stopcock valves allow for manual introduction and quick shutoff of fluid flow into the fluid injection ports 602, but in some embodiments it may be desirable to supplement or replace these stopcock valves with bullet valves 616 located at the bottom of port(s) 602, which can prevent "dripping" or leaking of fluid into the fluid injection port 602 (and thus into the electrode column) after fluid flow into the port 602 has ceased (e.g. by removing an interconnection of the fluid injection port 602 to an external source of fluid or by closing a stopcock valve associated with the fluid injection port 602).

Figure 12B:
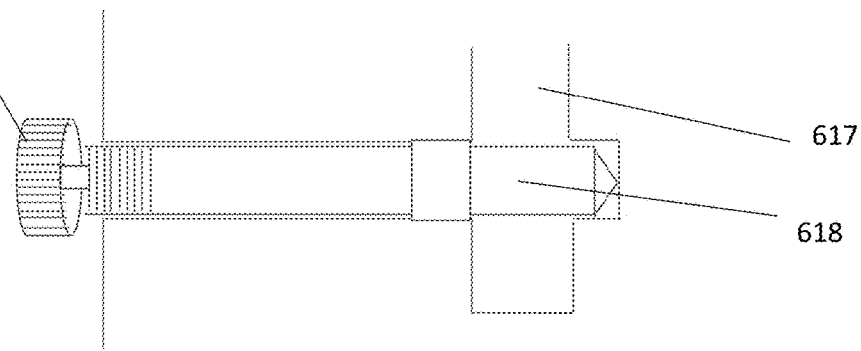
FIG. 12B is a cross-sectional detail of the needle or bullet valves of the acrylic block sensor assembly of FIG. 12A.

Referring now to FIG. 12B, a detail of the bullet valve 616 is illustrated. Particularly, the bullet valve 616 may prevent dripping or leaking in the port 602 by physical blockage of a fluid flow bore 617 of the fluid injection port 602 by a central shaft 618 of the bullet valve 616. As is apparent from FIG. 12B, the bullet valve 616 may be operable not only to isolate/shut off fluid flow through a port 602 completely (by maximally tightening the valve 616/inserting the shaft 618), but may also be operable to partially restrict fluid flow through the port 602 (by partially tightening the valve 616/inserting the shaft 618).

Figure 13A:
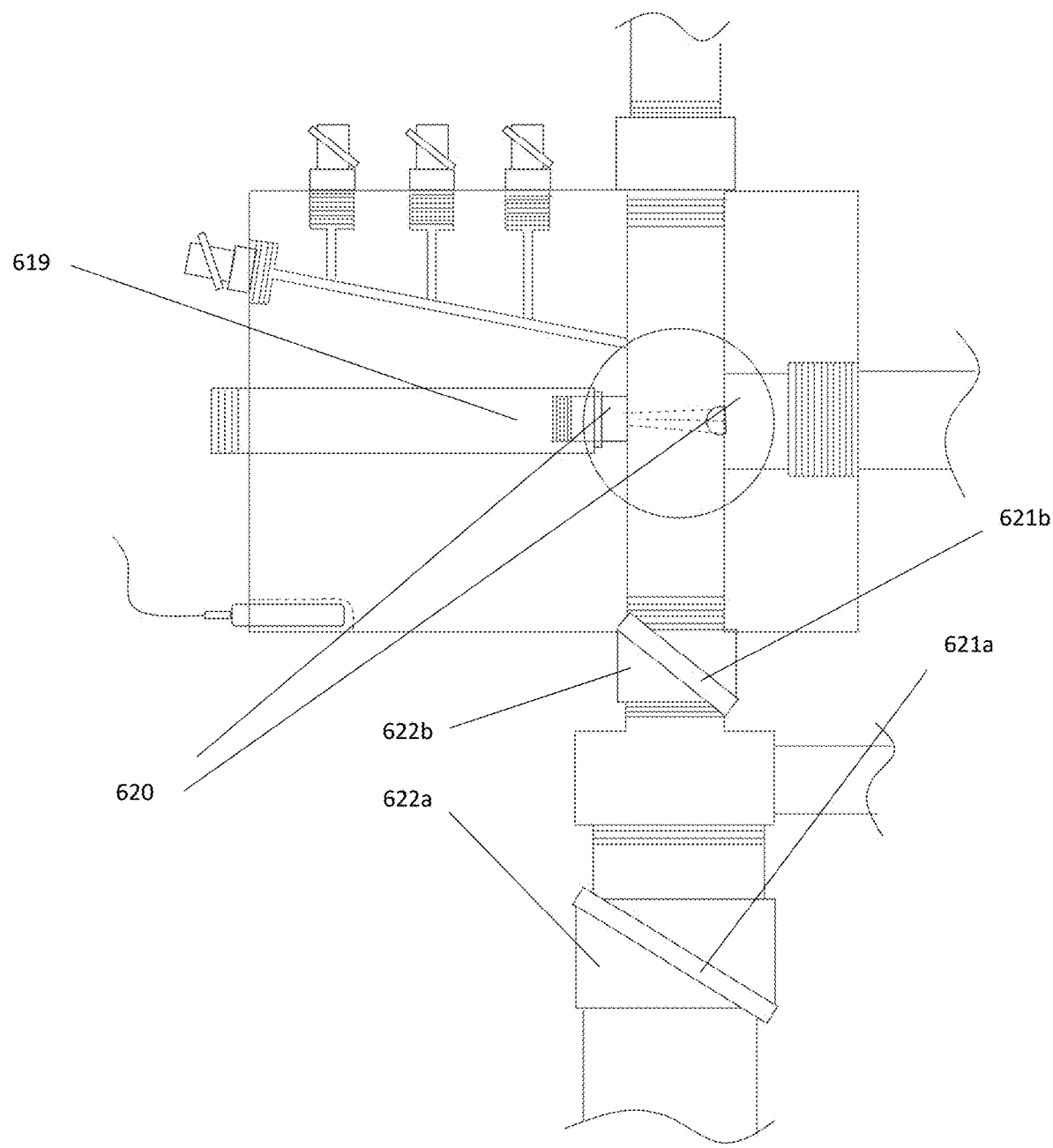
FIG. 13A is a perspective view of a sensor assembly illustrating the location and number of operating valves, according to embodiments of the present invention.

Referring now to FIG. 13A, the location and number of valves in embodiments of the invention are illustrated in further detail. In the embodiment illustrated in FIG. 13A, only two operating valves—a column isolation valve 621a and a drain valve 621b, mounted within the same connection line—are needed to isolate the device for a cleaning and calibration procedure. The cleaning or calibration cycle can be initiated by actuating the column isolation valve 621a to cause the aqueous analyte stream to be drained out of the assembly block 601 via the shared connection line. Simultaneously with or subsequent to actuation of the column isolation valve 621a, the drain valve 621b is actuated to cause any fluid (i.e. analyte) remaining in the electrode column to drain out of the assembly block 601 via the shared connection line. The column isolation valve 621a and the drain valve 621b thus serve much the same purpose as the valves of the main and secondary drain assemblies 412,413 of the embodiment illustrated in FIG. 2.

As illustrated in FIG. 13A, the diameter of the shared connection line at the valve connection 622a associated with the column isolation valve 621a may be larger than the diameter of the shared connection line at the valve connection 622b associated with the drain valve 622b. Such a change in the pipe diameter allows the continuous flow of the aqueous analyte stream out of the assembly block 601 during a cleaning or calibration mode, thus eliminating the need to cease or shut off flow of the aqueous analyte stream to the assembly block 601 and guaranteeing that the electrode tip will receive a "fresh" analyte sample when the cleaning/calibration cycle is completed and the system is returned to normal measurement operations, and reduces the necessary number of connections and operating valves.

Figure 13B:
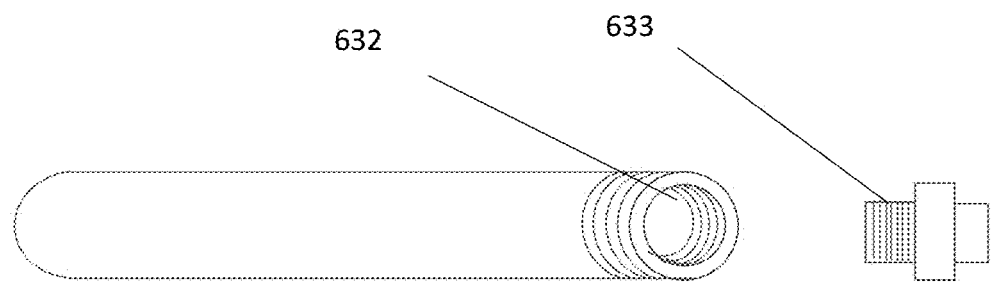
FIG. 13B is an illustration of a pipe connection to a potable water spray diffuser, according to embodiments of the present invention.

FIG. 13A also illustrates how the spray diffusers 606,611,614 may be "press-fit" into the assembly block 601. Particularly, as illustrated with regard to central diffuser 611, an external threaded connection of the diffuser 611 may mate with a portion 620 of a pipe connection 619 that has threads on an internal surface, i.e. to receive a portion of the diffuser 611 within the pipe connection 619. The same portion 620, or a different portion, of the pipe connection 619 also has threads on an external surface, which mate with corresponding threads machined into a wall of the electrode column or another proximal portion of the assembly block 601. Thus, a sealed diffuser assembly is provided, with an end of the spray diffuser 611 press-fitting into the assembly block 601 and being flush with a sidewall of the electrode column. As illustrated in FIG. 13A, the electrode itself and/or the sensor as a whole may be "press-fit" within the assembly block 601 by a similar type of threaded connection 620. This threaded connection may comprise a female threaded portion 632 on the pipe connection 619 and a male threaded portion 633 on the diffuser 611, as illustrated in FIG. 13B.

Figure 14A:
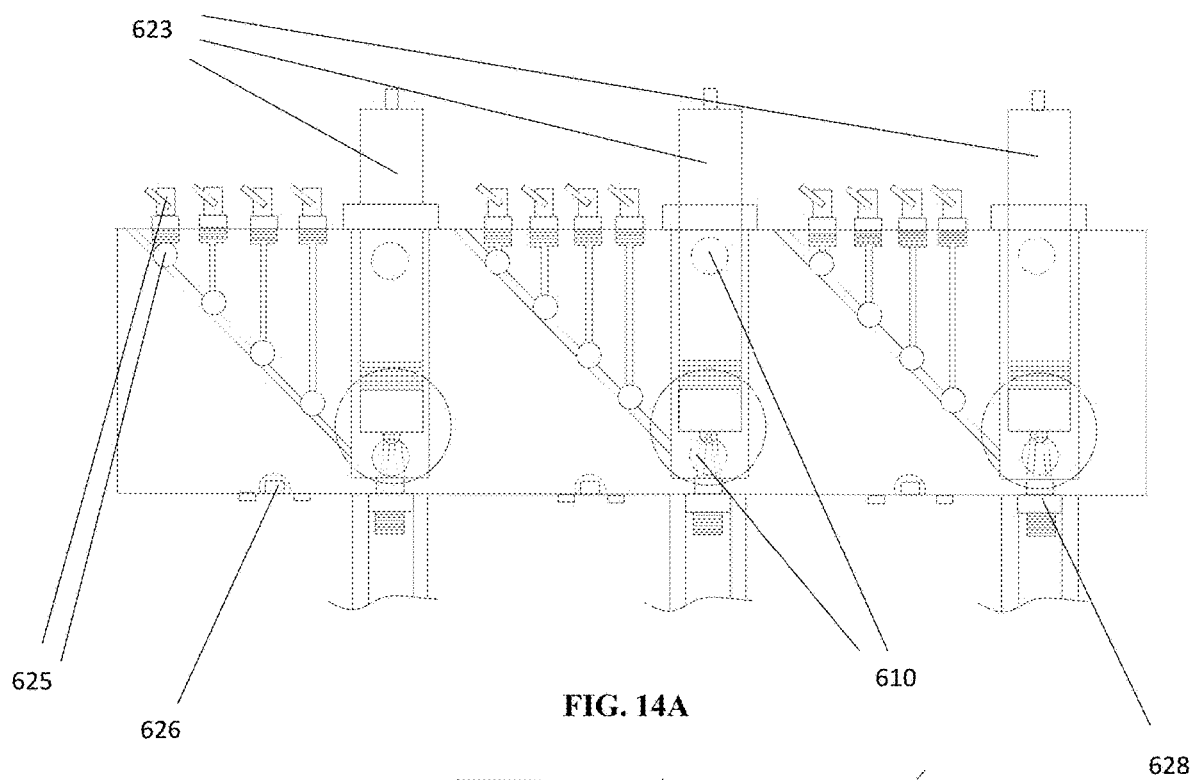
FIGS. 14A and 14B are perspective views of a sensor assembly machined from a single acrylic block that can accommodate multiple sensors, according to embodiments of the present invention.
Figure 14B:
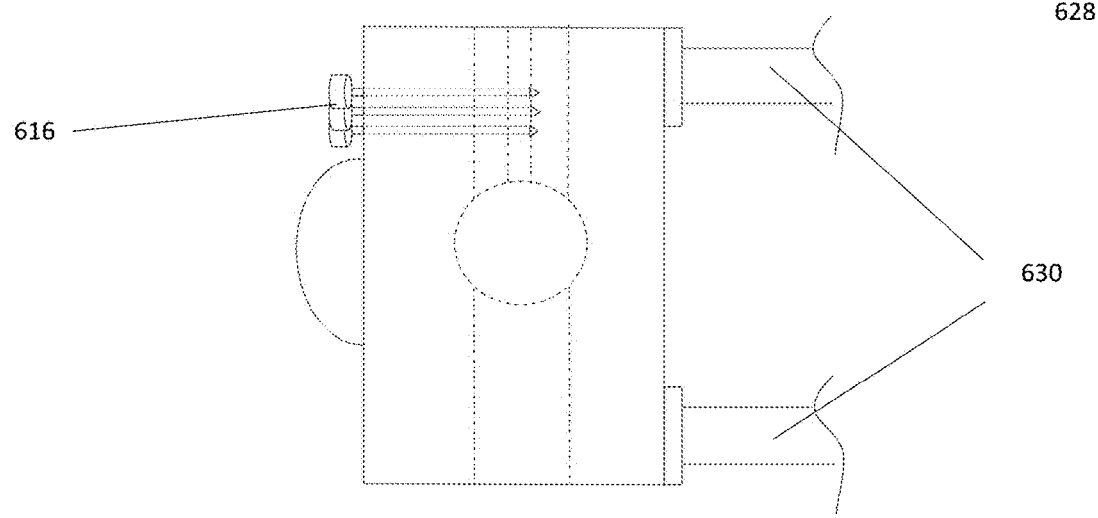

Referring now to FIGS. 14A and 14B, a perspective view of an assembly block 601 configured for use with multiple sensors and a detail thereof, respectively, are illustrated. In the embodiment illustrated in FIGS. 14A and 14B, numerous sensors 623, in this case pH sensors (but conceivably any type of sensors having a roughly cylindrical shape), or at least the electrodes thereof are mounted within individual electrode columns of the assembly block 601 by any suitable fluid-tight mounting or interconnection as known in the art or as described herein. Fluid injection ports 602, which interconnect with a separate internal manifold 603 associated with each sensor 623 are provided with either stopcock valves 625 at the top of the assembly block 601 (as illustrated in FIG. 14A) or bullet valves 616 in a machined slot at the bottom of the fluid injection port(s) 602 (as illustrated in FIG. 14B); in some embodiments, bullet/stem type needle valves 616 may be preferable to prevent "dripping" or leaking of fluid after shutoff. In this embodiment, LED lighting 626 is provided and held within within a machined slot of the assembly block 601; the mounting of the LED lighting 626 is achieved by attaching a steel plate, disposed on the bottom of the LED lighting, to the assembly block 601 by screws, and further including on the bottom of the LED lighting 626 a magnetic strip to hold the LED lighting 626 in place. As in the embodiment illustrated in FIG. 11A, inlet and outlet connection(s), e.g. fluid connections 610, 630, are disposed on a rear aspect of the assembly block 601 to accommodate the mounting of the spray diffusers. A fresh or potable water inlet assembly 628 is provided in association with each electrode column. This configuration may be particularly useful in applications in which the space available for installation of the device is limited.

Figure 15:
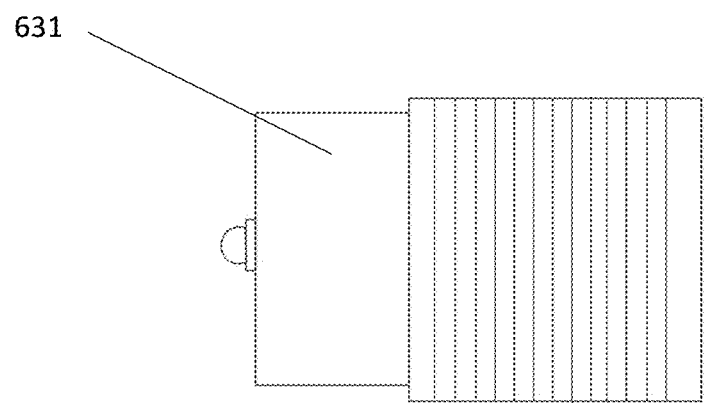
FIG. 15 is an illustration of a sensor cap or holder material, according to embodiments of the present invention.

Referring now to FIG. 15, a cap or holder material 631 for a sensor 623 is illustrated. The cap 631 is preferably made from a chemically resistant, non-stick/low-friction material such as PTFE. As before, the sensor end may be manufactured to allow for a press-fit installation into the acrylic or similar plastic material of the assembly block 601 that aligns with a sidewall of the electrode column.

Figure 16A:
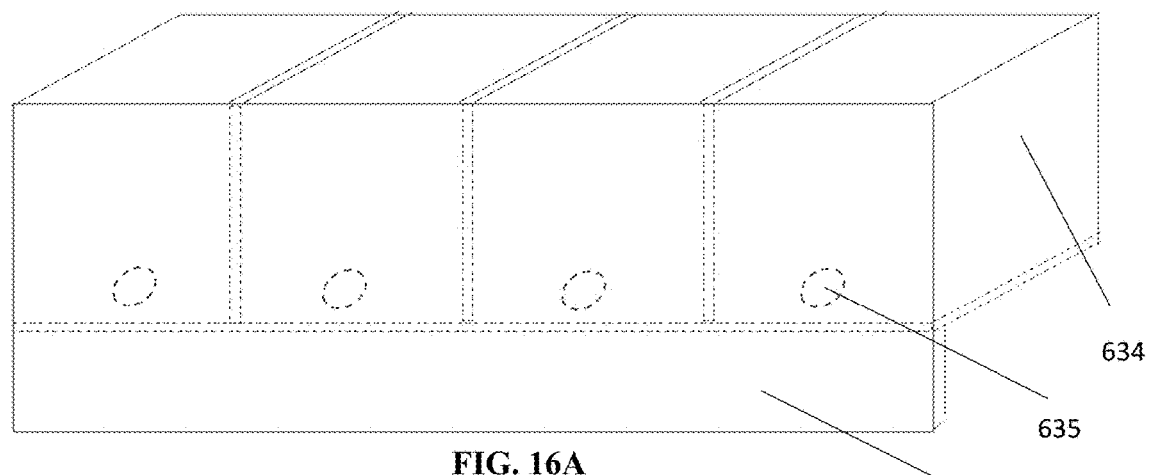
FIG. 16A is a perspective view of a chemical storage system, according to embodiments of the present invention.
Figures 16B, 16C:
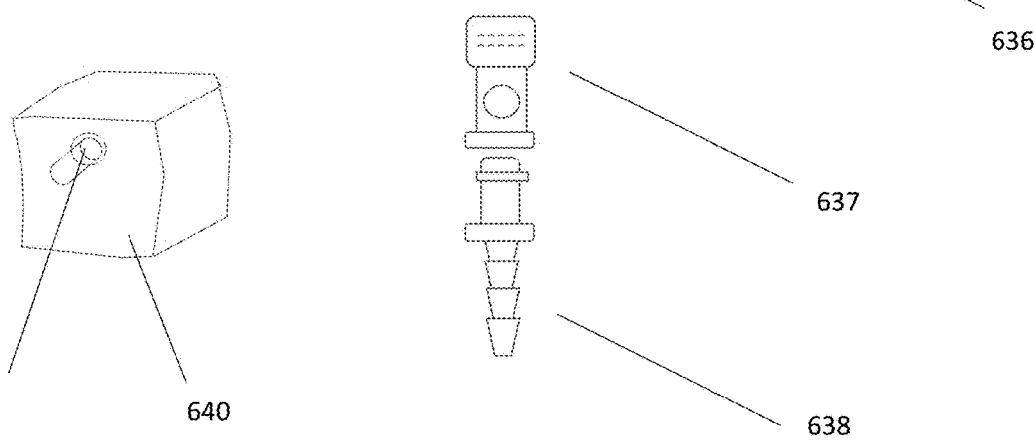
FIGS. 16B and 16C are perspective views of chemical storage connections, according to embodiments of the present invention.

Referring now to FIGS. 16A through 16C, a chemical storage assembly of the present invention, suitable for storing cleaning or calibration fluids and the like for use in conjunction with devices of the present invention, is illustrated. The chemical storage assembly is preferably constructed of chemically resistant materials, including but not limited to acrylic or similar plastic materials from which the assembly blocks 402/601 may be made. The chemical storage assembly is sealed to be fluid-tight and is non-vented to prevent oxidation or other chemical degradation of chemicals within the chemical storage assembly due to contact with air or other ambient materials. In some embodiments, the chemical storage assembly may be compartmentalized into multiple independently collapsible containers 634, which may take the shape of rectangular prisms and particularly of cubes. Preferably, at least one container 634 of the chemical storage assembly is fitted with a connecting portion 635, and preferably a connector 639 on a lower front aspect 640 of the container 634; the connector 639, in turn, preferably comprises a valved, chemically resistant seal 637 that interfaces with a connector 638 of, e.g., a fluid injection port 602 of a device of the present invention and maintains a fluid-tight seal of the container 634 when not connected. Additionally, as an added safety precaution (e.g. to prevent risk of eye injury to operators or technicians when disconnecting a connector 639), the chemical storage assembly may comprise a face plate 635 that extends below the connectors 639 and is manufactured of a transparent or translucent material to allow for visual inspection of the chemicals within a container 634.

Figure 17A:
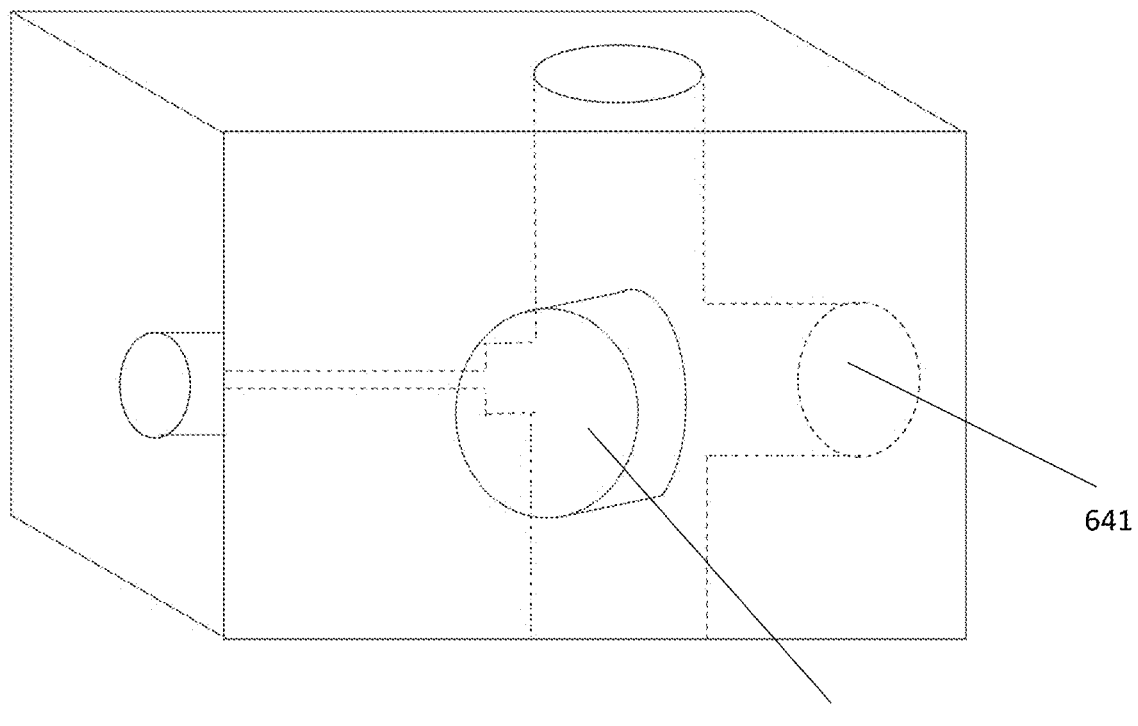
FIGS. 17A and 17B are perspective views of an angled machine mounting of a sensor and a magnifying lens, according to embodiments of the present invention.
Figure 17B:
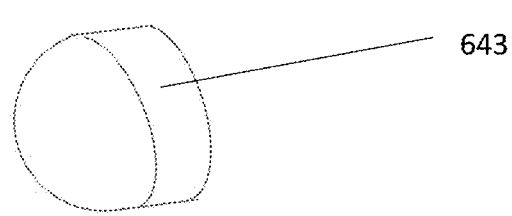

Referring now to FIGS. 17A and 17B, a sensor mounting 641 and/or a magnifying lens mounting 642 may be disposed at an angle relative to each other and/or to a surrounding portion of the assembly block 601. Particularly, a sensor electrode tip may be flush with an end of the sensor, i.e. may not protrude beyond a sensor housing or other longitudinal portion of the sensor; in this case, visual inspection of the electrode tip can be facilitated by angling the electrode tip and/or magnifying lens 643 relative to each other to make the electrode tip more visible to the magnifying lens. In these embodiments, a distance between the magnifying lens 643 and the electrode tip and a magnification of the magnifying lens 643 may be selected in conjunction with each other to provide a desired overall magnifying effect; by way of non-limiting example, a distance between the magnifying lens 643 and a center of the electrode tip may preferably be between about 0.8 inches and about 1.0 inches and the magnifying lens may have a magnification of about 4×.

Figure 18:
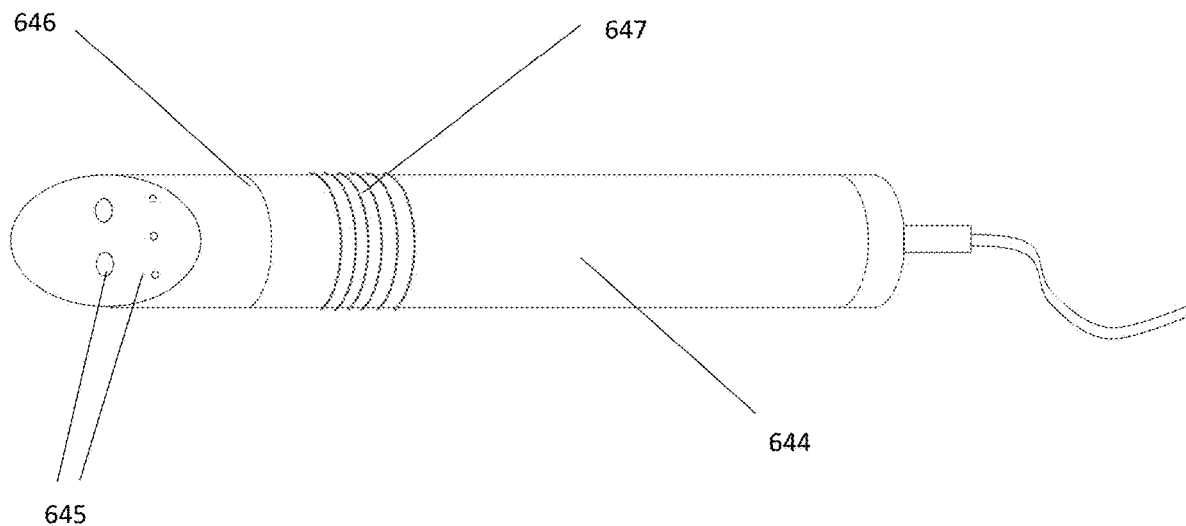
FIG. 18 is an illustration of a sensor assembly including sensors that have flush-mounted electrodes/diodes to employ an angled end or "cap," according to embodiments of the present invention.

Referring now to FIG. 18, a sensor having an angled tip 645 is illustrated. In this embodiment, the electrode tip 645 is mounted flush with an end of a cylindrical sensor body 644, which prevents inspection of the electrode tip 645 by a magnifying lens 643 (or other visual inspection device) unless the electrode tip 645 and magnifying lens 643 are mounted at an angle relative to each other, as illustrated in FIG. 17A. As illustrated in FIG. 18, the sensor may also include a detachable cap 646 made of PTFE or similarly chemically resistant material (which may be the same as or different from cap 631 illustrated in FIG. 15) and mounting threads 647 that allow for installation of the sensor body 644 into a pipe or assembly that possesses complementary threads.

A number of variations and modifications of the disclosure can be used. It would be possible to provide for some features of the disclosure without providing others.

The present disclosure, in various aspects, embodiments, and configurations, includes components, methods, processes, systems and/or apparatus substantially as depicted and described herein, including various aspects, embodiments, configurations, sub-combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspect, embodiment, or configuration. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. By way of first non-limiting example, various valves are described herein as either solenoid (i.e. electrically actuated) valves or manual (i.e. mechanically actuated) valves, and it is to be expressly understood that, unless otherwise specified, solenoid valves may be replaced with manual valves and vice versa, without departing from the scope of the present invention. Solenoid valves may also be replaced with motorized or otherwise automated valves. Similarly and by way of second non-limiting example, unless otherwise specified, any method or process described herein as "manual" may be partially or completely implemented by a programmable logic controller or microprocessor and thus be practiced as a "semi-automated" or "automated" method, and any method or process described herein as "semi-automated" or "automated" may be implemented by a user or technician and thus be practiced as a "manual" method, without departing from the scope of the present invention.

The invention claimed is:

1. A sensor cleaning and calibration system, comprising:
a sensor holder assembly, comprising a block of solid plastic material, configured to receive and securely hold a sensor electrode by a mechanical interconnection, wherein the sensor electrode comprises an electrode tip and is configured to measure a parameter of a stream of an aqueous analyte, wherein the block of solid plastic material surrounds and defines an electrode column, the electrode column being configured to house the electrode tip of the sensor electrode;
an analyte inlet for receiving the aqueous analyte stream;
an analyte outlet for discharging the aqueous analyte stream;
a check valve associated with the analyte inlet, configured to prevent backflow of the aqueous analyte stream;
a main drain assembly, comprising a first drain valve, wherein the first drain valve is reconfigurable between an actuated configuration and a non-actuated configuration, wherein the first drain valve allows the aqueous analyte stream to flow into the electrode column when in the non-actuated configuration and drains the aqueous analyte stream away from the electrode column when in the actuated configuration;
a secondary drain assembly, comprising a second drain valve, wherein the second drain valve is reconfigurable between an actuated configuration and a non-actuated configuration, wherein the second drain valve allows aqueous analyte to be retained in the electrode column and at least partially surround the electrode tip when in the non-actuated configuration and drains the electrode column of aqueous analyte when in the actuated configuration;
a cleaning or calibration fluid inlet, adapted to receive a cleaning or calibration fluid;
a spray/fill diffuser, operable to spray or flow the received cleaning or calibration fluid into the electrode column to clean or calibrate the sensor electrode or a portion thereof; and
an ultrasonic transducer disposed proximal to the electrode tip and configured to provide an ultrasonic cleaning function to the sensor electrode.

2. A sensor cleaning and calibration system, comprising:
a sensor holder assembly, comprising a block of solid plastic material, configured to receive and securely hold a sensor electrode by a mechanical interconnection, wherein the sensor electrode comprises an electrode tip and is configured to measure a parameter of an aqueous analyte, wherein the block of solid plastic material surrounds and defines an electrode column, the electrode column being configured to house the electrode tip and having at least one sidewall;
a column isolation assembly, comprising a column isolation valve, wherein the column isolation valve is reconfigurable between an actuated configuration and a non-actuated configuration, wherein the column isolation valve allows the aqueous analyte stream to flow into the electrode column when in the non-actuated configuration and directs the aqueous analyte stream away from the electrode column when in the actuated configuration;
a drain assembly, comprising a drain valve, wherein the drain valve is reconfigurable between an actuated configuration and a non-actuated configuration, wherein the drain valve allows aqueous analyte to be retained in the electrode column and at least partially surround the electrode tip when in the non-actuated configuration and drains the electrode column of aqueous analyte when in the actuated configuration;
at least one fluid injection port, each fluid injection port comprising a selectively reconfigurable valve;
an internal chemical manifold, in fluid communication with the at least one fluid injection port; and
upper, central, and lower spray diffusers, configured to receive fluid from the internal chemical manifold and spray fluid within the electrode column,
wherein a spray pattern of the central spray diffuser is narrower than a spray pattern of at least one of the upper spray diffuser and the lower spray diffuser, wherein the upper and lower spray diffusers are configured to spray fluid on at least a portion of the at least one sidewall of the electrode column and the central spray diffuser is configured to spray fluid on at least a portion of the electrode tip, and wherein diffuser surfaces of the upper, central, and lower spray diffusers are substantially flush with the at least one sidewall of the electrode column.

3. The system of claim 2, wherein the mechanical interconnection comprises a threaded or socket connection.

4. The system of claim 2, further comprising a visual inspection device, mounted on or within the sensor holder assembly and positioned to enable a user to visually inspect the electrode tip.

5. The system of claim 2, wherein the selectively reconfigurable valve is selected from the group consisting of a stopcock valve and a bullet valve.

6. The system of claim 2, wherein a diameter of the spray pattern of the central spray diffuser is between about 90% and about 120% of a diameter of the electrode tip.

7. The system of claim 2, wherein at least a portion of an outer surface of at least one of the upper spray diffuser, the central spray diffuser, and the lower spray diffuser is constructed of polytetrafluoroethylene.

8. The system of claim 2, further comprising a light-emitting diode configured to provide a visual indicator of an operating condition of the system.

9. The system of claim 2, wherein the sensor electrode comprises an electrode cap.

10. The system of claim 2, wherein the parameter is selected from the group consisting of pH, dissolved oxygen content, ammonia content, chlorine content, monochloramine content, ozone content, total suspended solid content, mixed liquor suspended solid content, and ultraviolet transmittance.

11. The system of claim 2, further comprising a non-transitory computer-readable medium storing instructions that, when executed by a computer processor, cause the computer processor to initiate a cleaning or calibration procedure by performing the steps of:
actuating the column isolation valve;
actuating the drain valve; and
activating at least one of the upper spray diffuser, the central spray diffuser, and the lower spray diffuser.

12. A sensor cleaning and calibration system, comprising:

a sensor holder assembly, comprising a block of solid plastic material, configured to receive and securely hold a sensor electrode by a mechanical interconnection, wherein the mechanical interconnection comprises a threaded or socket connection, wherein the sensor electrode comprises an electrode tip and is configured to measure a parameter of a stream of an aqueous analyte, wherein the parameter is selected from the group consisting of pH, dissolved oxygen content, ammonia content, chlorine content, monochloramine content, ozone content, total suspended solid content, mixed liquor suspended solid content, and ultraviolet transmittance, wherein the block of solid plastic material surrounds and defines an electrode column, the electrode column being configured to house the electrode tip of the sensor electrode;

an analyte inlet for receiving the aqueous analyte stream;

an analyte outlet for discharging the aqueous analyte stream;

a check valve associated with the analyte inlet, configured to prevent backflow of the aqueous analyte stream;

a main drain assembly, comprising a first drain valve, wherein the first drain valve is reconfigurable between an actuated configuration and a non-actuated configuration, wherein the first drain valve allows the aqueous analyte stream to flow into the electrode column when in the non-actuated configuration and drains the aqueous analyte stream away from the electrode column when in the actuated configuration;

a secondary drain assembly, comprising a second drain valve, wherein the second drain valve is reconfigurable between an actuated configuration and a non-actuated configuration, wherein the second drain valve allows aqueous analyte to be retained in the electrode column and at least partially surround the electrode tip when in the non-actuated configuration and drains the electrode column of aqueous analyte when in the actuated configuration;

a cleaning or calibration fluid inlet, adapted to receive a cleaning or calibration fluid;

a spray/fill diffuser, operable to spray or flow the received cleaning or calibration fluid into the electrode column to clean or calibrate the sensor electrode or a portion thereof;

a visual inspection device, mounted on or within the sensor holder assembly and positioned to enable a user to visually inspect the electrode tip;

means for receiving a stream of fresh or potable water, wherein the spray/fill diffuser is operable to spray or rinse the sensor electrode or a portion thereof with the received fresh or potable water;

a manual fluid injection port, comprising a lock fitting and a manual valve, configured to receive and dispense into the electrode column a manually administered aliquot of the cleaning or calibration fluid; and an ultrasonic transducer disposed proximal to the electrode tip and configured to provide an ultrasonic cleaning function to the sensor electrode.

* * * * *